US012778970B2

(12) United States Patent
Barron et al.

(10) Patent No.: US 12,778,970 B2
(45) Date of Patent: Nov. 3, 2026

(54) SUBSTITUTED RESORCYLIC ACID COMPOUNDS AS AMPK ACTIVATOR AND USES THEREOF

(71) Applicant: SOCIETE DES PRODUITS NESTLE S.A., Vevey (CH)

(72) Inventors: Denis Marcel Barron, Lutry (CH); Olivier Ciclet, Lonay (CH); Martine Naranjo Pinta, Morges (CH); Katyayanee Neopane, Preverenges (CH); Yann Ratinaud, Morges (CH); Matthew Sanders, Epalinges (CH)

(73) Assignee: Societe des Produits Nestle S.A., Vevey (CH)

( * ) Notice: Subject to any disclaimer, the term of this patent is extended or adjusted under 35 U.S.C. 154(b) by 437 days.

(21) Appl. No.: 18/251,759

(22) PCT Filed: Nov. 2, 2021

(86) PCT No.: PCT/EP2021/080298
§ 371 (c)(1),
(2) Date: May 4, 2023

(87) PCT Pub. No.: WO2022/096423
PCT Pub. Date: May 12, 2022

(65) Prior Publication Data

US 2023/0414638 A1 Dec. 28, 2023

(30) Foreign Application Priority Data

Nov. 5, 2020 (EP) .................................... 20205952

(51) Int. Cl.
*A61P 1/16* (2006.01)
*A61K 31/00* (2006.01)

(52) U.S. Cl.
CPC .............. *A61K 31/658* (2023.05); *A61P 1/16* (2018.01)

(58) Field of Classification Search
CPC ................................ A61K 31/658; A61P 1/16
USPC .......................................................... 514/568
See application file for complete search history.

(56) References Cited

FOREIGN PATENT DOCUMENTS

| | | | | |
|---|---|---|---|---|
| EP | 2796442 | | 10/2014 | |
| WO | 0213806 | | 2/2002 | |
| WO | 0213811 | | 2/2002 | |
| WO | 2012144892 | | 10/2012 | |
| WO | WO-2012144892 | A1 * | 10/2012 | ............. A61P 43/00 |
| WO | 2019228794 | | 12/2019 | |
| WO | 2020186010 | | 9/2020 | |
| WO | 2021028917 | A1 | 2/2021 | |
| WO | 2021245671 | A1 | 12/2021 | |
| WO | 2021245672 | A1 | 12/2021 | |

OTHER PUBLICATIONS

Xu et al. "Neuroprotective effect of cajaninstilbene acid against cerebral ischemia and reperfusion damages by activating AMPK/Nrf2 pathway" Journal of Advanced Research, 2021, vol. 34, pp. 199-210.
Weidner et al. "Amorfrutins are potent antidiabetic dietary natural products" PNAS, May 8, 2012, vol. 109, No. 19, pp. 7257-7262.
Fellous et al. "Phytocannabinoids promote viability and functional adipogenesis of bone marrow-derived mesenchymal stem cells through different molecular targets" Biochemical Pharmacology, 2020, vol. 175, 13 pages.
European Office Action for Appl No. 21 798 399.8-1109 dated Aug. 21, 2024, 14 pages.
European Office Action for Appl No. 21 798 399.8-1109 dated Apr. 25, 2025, 5 pages.
Wang et al., "Cannabidiol Attenuates Alcohol-Induced Liver Steatosis, Metabolic Dysregulation, Inflammation and Neutrophil-Mediated Injury", Scientific Reports, vol. 7, Issue No. 1, Sep. 21, 2017, pp. 1-12, XP093412013.
"Steatotic (Fatty) Liver Disease", Cleveland Clinic, Retrived from <https://my.clevelandclinicorg/health/diseases/15831-fatty-liver-disease>, Sep. 27, 2023, 05 Pages, XP093412601.
European Search Report for Appl No. 26165504.7-1109 dated Jul. 8, 2026, 8 pages.

* cited by examiner

*Primary Examiner* — Yevgeny Valenrod
(74) *Attorney, Agent, or Firm* — K&L Gates LLP

(57) ABSTRACT

The present invention relates to a substituted resorcylic acid compound having general formula I and compositions comprising said compound for use in the activation of AMPK. The compounds are useful for the treatment or prevention of a condition, disorder or disease related to type 2 diabetes, non-alcoholic fatty liver disease and/or obesity.

8 Claims, 4 Drawing Sheets

SUBSTITUTED RESORCYLIC ACID COMPOUNDS AS AMPK ACTIVATOR AND USES THEREOF

CROSS REFERENCE TO RELATED APPLICATIONS

The present application is a National Stage of International Application No. PCT/EP2021/080298, filed on Nov. 2, 2021, which claims priority to European Patent Application No. 20205952.3, filed on Nov. 5, 2020, the entire contents of which are being incorporated herein by reference.

INTRODUCTION

AMP-activated protein kinase (AMPK) is an evolutionarily conserved master regulator of energy homeostasis that coordinates metabolic pathways in order to balance nutrient supply with energy demand. AMPK is considered a key drug target to combat the growing epidemic of metabolic disorders such as obesity, type 2 diabetes, cardiovascular disease.

AMPK activity is found in all tissues, including liver, kidney, muscle, lung, and brain (PMID: 10698692). In terms of structure, AMPK is a heterotrimeric complex consisting of a catalytic subunit (α) and two regulatory subunits (β and γ). The AMPK complex is evolutionarily conserved and also can be found in yeast and plants. Mammalian AMPK is composed of different isoforms of subunits: α1, α2, β1, β2, γ1, γ2, and γ3 (PMID: 11746230) leading to 12 possible heterotrimeric combinations. The α2 isoform is predominately found in skeletal and cardiac muscle AMPK; both the α1 and α2 isoforms are found in hepatic AMPK; while for example in adipose and T cells the α1 isoform AMPK predominates (PMID: 16818670, PMID 15878856).

There is no direct AMPK-activating drug available to treat metabolic disorders despite intensive efforts continuously made by the pharmaceutical industry. Several synthetic AMPK activators have been identified/developed. However, they either have no/poor oral availability (PMID: 16753576, PMID: 24900234) or there are concerns about their off-target, adverse effects, since chronic and strong AMPK activation may cause increases in cardiac glycogen content and hypertrophy (PMID: 11827995).

Finding natural bioactive molecules that moderately activate AMPK especially in muscle, liver and kidney with defined mechanism of action are likely to provide exercise-mimetic effects and help maintain/improve metabolic health.

There are numerous natural compounds/extracts known to bring about some metabolic health benefits that are shown to indirectly stimulate AMPK most likely through inhibition of mitochondrial respiration. However, whether those metabolic effects are mediated by AMPK is largely elusive, and moreover there are concerns regarding side/toxic effects such as cellular or mitochondrial poisoning.

There is a clear unmet need for new natural compounds which directly activate AMPK.

SUMMARY OF INVENTION

Numerous studies have demonstrated that a wide range of different natural compounds activate AMPK. However, typically, natural compounds do not activate AMPK by directly binding to the enzyme, but instead indirectly activate AMPK by causing perturbations in mitochondrial respiration. This leads to a decrease in ATP levels of the cell and activation of AMPK through AMP/ADP binding to the nucleotide-binding site of the AMPK γ subunit.

In contrast, in the present invention, we have identified natural compounds that bind directly to AMPK through the allosteric drug and metabolite (ADaM) site formed at the interface between the AMPK α and AMPK β subunits. These compounds are from the class of substituted resorcyclic acids and directly activate AMPK in cells.

The invention relates to a compound having the general formula (I), (I)

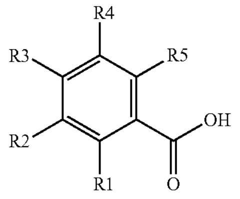

wherein R1 and R3 are each independently OH; OCH3; O-aliphatic saturated or unsaturated acyl, O-glycoside; acylated O-glycoside; sulfated O-glycoside; or a sulfate;

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl;

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl;

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK; optionally a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C10 polyalkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C10 polyalkenyl; an optionally substituted and/or optionally branched C2 to C20 alkynyl, or an optionally substituted and/or optionally branched C4 to C20 polyalkynyl.

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C10 polyalkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C10 to C20 alkenyl; an optionally substituted and/or optionally branched, C10 to C20 polyalkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; an optionally branched C1 to C20 alkyl; an optionally branched, C2 to C20 alkenyl; an optionally branched, C4 to C20 polyalkenyl; an optionally branched C2 to C20 alkynyl, or an optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C10 to C20 alkenyl; an optionally substituted and/or optionally branched, C10 to C20 polyalkenyl; an optionally substituted and/or optionally branched C2 to C20 alkynyl, or an optionally substituted and/or optionally branched C4 to C20 polyalkynyl.

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; an optionally branched C1 to C20 alkyl; an optionally branched, C2 to C20 alkenyl; an optionally branched, C4 to C20 polyalkenyl; an optionally branched C2 to C20 alkynyl, or an optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C10 to C20 alkenyl; an optionally substituted and/or optionally branched, C10 to C20 polyalkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; an optionally branched C1 to C20 alkyl; an optionally branched, C2 to C20 alkenyl; an optionally branched, C4 to C20 polyalkenyl; an optionally branched C2 to C20 alkynyl, or an optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside. sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C10 to C20 alkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; an optionally branched C1 to C20 alkyl; an optionally branched, C2 to C20 alkenyl; an optionally branched, C4 to C20 polyalkenyl; an optionally branched C2 to C20 alkynyl, or an optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C10 to C20 alkenyl; an optionally substituted and/or optionally branched C2 to C20 alkynyl, or an optionally substituted and/or optionally branched C4 to C20 polyalkynyl.

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; an optionally branched C1 to C20 alkyl; an optionally branched, C2 to C20 alkenyl; an optionally branched, C4 to C20 polyalkenyl; an optionally branched C2 to C20 alkynyl, or an optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C10 to C20 alkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; an optionally branched C1 to C20 alkyl; an optionally branched, C2 to C20 alkenyl; an optionally branched, C4 to C20 polyalkenyl; an optionally branched C2 to C20 alkynyl, or an optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 and R5 are each independently H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C10 polyalkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C10 polyalkenyl; an optionally substituted and/or optionally branched C2 to C20 alkynyl, or an optionally substituted and/or optionally branched C4 to C20 polyalkynyl.

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C10 polyalkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C10 to C20 alkenyl; an optionally substituted and/or optionally branched, C10 to C20 polyalkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally branched C1 to C20 alkyl; an optionally branched, C2 to C20 alkenyl; an optionally branched, C4 to C20 polyalkenyl; an optionally branched C2 to C20 alkynyl, or an optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C10 to C20 alkenyl; an optionally substituted and/or optionally branched, C10 to C20 polyalkenyl; an optionally substituted and/or optionally branched C2 to C20 alkynyl, or an optionally substituted and/or optionally branched C4 to C20 polyalkynyl.

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally branched C1 to C20 alkyl; an optionally branched, C2 to C20 alkenyl; an optionally branched, C4 to C20 polyalkenyl; an optionally branched C2 to C20 alkynyl, or an optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C10 to C20 alkenyl; an optionally substituted and/or optionally branched, C10 to C20 polyalkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally branched C1 to C20 alkyl; an optionally branched, C2 to C20 alkenyl; an optionally branched, C4 to C20 polyalkenyl; an optionally branched C2 to C20 alkynyl, or an optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C10 to C20 alkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally branched C1 to C20 alkyl; an optionally branched, C2 to C20 alkenyl; an optionally branched, C4 to C20 polyalkenyl; an optionally branched C2 to C20 alkynyl, or an optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C10 to C20 alkenyl; an optionally substituted and/or optionally branched C2 to C20 alkynyl, or an optionally substituted and/or optionally branched C4 to C20 polyalkynyl.

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally branched C1 to C20 alkyl; an optionally branched, C2 to C20 alkenyl; an optionally branched, C4 to C20 polyalkenyl; an optionally branched C2 to C20 alkynyl, or an optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally substituted and/or optionally branched C1 to C20 alkyl; an optionally substituted and/or optionally branched, C10 to C20 alkenyl; an optionally substituted and/or optionally branched C2 to C20 alkynyl, or an optionally substituted and/or optionally branched C4 to C20 polyalkynyl.

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl.

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; an optionally branched C1 to C20 alkyl; an optionally branched, C2 to C20 alkenyl; an optionally branched, C4 to C20 polyalkenyl; an optionally branched C2 to C20 alkynyl, or an optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is CH3, OH; O-glycoside; C-glycoside; sulfated O-glycoside; sulfated C-glycoside; a chlorine; a CHO (aldehyde); a sulfate; an optionally substituted and/or optionally branched, C2 to C15 alkenyl; or an optionally substituted and/or optionally branched, C4 to C15 polyalkenyl.

R4 is H; CH3, OH; OCH3; a chlorine, or a 3,3-dimethylallyl chain (1h).

R5 is H; an optionally substituted and/or optionally branched C1 to C20 alkyl; an optionally substituted and/or optionally branched, C2 to C20 alkenyl; or an optionally substituted and/or optionally branched, C4 to C20 polyalkenyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; CH3, OH; O-glycoside; C-glycoside; sulfated O-glycoside; sulfated C-glycoside; a chlorine; a CHO (aldehyde); a sulfate; an optionally substituted and/or optionally branched, C2 to C15 alkenyl; or an optionally substituted and/or optionally branched, C4 to C15 polyalkenyl.

R4 is CH3, OH; OCH3; a chlorine; or a 3,3-demethylallyl chain (1h).

R5 is H; an optionally substituted and/or optionally branched C1 to C20 alkyl; an optionally substituted and/or optionally branched, C2 to C20 alkenyl; or an optionally substituted and/or optionally branched, C4 to C20 polyalkenyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; CH3, OH; O-glycoside; C-glycoside; sulfated O-glycoside; sulfated C-glycoside; a chlorine; a CHO (aldehyde); a sulfate; an optionally substituted and/or optionally branched, C2 to C15 alkenyl; or an optionally substituted and/or optionally branched, C4 to C15 polyalkenyl.

R4 is H; CH3, OH; OCH3; a chlorine; or a 3,3-dimethylallyl chain (1h).

R5 is an optionally substituted and/or optionally branched C1 to C20 alkyl; an optionally substituted and/or optionally branched, C2 to C20 alkenyl; or an optionally substituted and/or optionally branched, C4 to C20 polyalkenyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is CH3, OH; O-glycoside; C-glycoside; sulfated O-glycoside; sulfated C-glycoside; a chlorine; a CHO (aldehyde); a sulfate; an optionally substituted and/or optionally branched, C2 to C20 alkenyl; or an optionally substituted and/or optionally branched, C4 to C10 polyalkenyl.

R4 is H; CH3, OH; OCH3; a chlorine; or a 3,3-dimethylallyl chain (1h).

R5 is H; an optionally substituted and/or optionally branched C1 to C20 alkyl; an optionally substituted and/or optionally branched, C2 to C20 alkenyl; or an optionally substituted and/or optionally branched, C4 to C20 polyalkenyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; CH3; OH; O-glycoside; C-glycoside; sulfated O-glycoside; sulfated C-glycoside; a chlorine; a CHO (aldehyde); a sulfate; an optionally substituted and/or optionally branched, C2 to C20 alkenyl; or an optionally substituted and/or optionally branched, C4 to C10 polyalkenyl.

R4 is CH3; OH; OCH3; a chlorine; or a 3,3-dimethylallyl chain (1h).

R5 is H; an optionally substituted and/or optionally branched C1 to C20 alkyl; an optionally substituted and/or optionally branched, C2 to C20 alkenyl; or an optionally substituted and/or optionally branched, C4 to C20 polyalkenyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; CH3; OH; O-glycoside; C-glycoside; sulfated O-glycoside; sulfated C-glycoside; a chlorine; a CHO (aldehyde); a sulfate; an optionally substituted and/or optionally branched, C2 to C20 alkenyl; or an optionally substituted and/or optionally branched, C4 to C10 polyalkenyl.

R4 is H; CH3; OH; a chlorine; or a 3,3-demethylallyl chain (1h).

R5 is an optionally substituted and/or optionally branched C1 to C20 alkyl; an optionally substituted and/or optionally branched, C2 to C20 alkenyl; or an optionally substituted and/or optionally branched, C4 to C20 polyalkenyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is CH3; OH; O-glycoside; C-glycoside; sulfated O-glycoside; sulfated C-glycoside; a chlorine; a CHO (aldehyde); a sulfate; an optionally substituted and/or optionally branched, C10 to C15 alkenyl; or an optionally substituted and/or optionally branched, C10 to C15 polyalkenyl.

R4 is H; CH3; OH; OCH3; a chlorine; or a 3,3-dimethylallyl chain (1h).

R5 is H; an optionally branched C1 to C20 alkyl; an optionally branched, C2 to C20 alkenyl; or an optionally branched, C4 to C20 polyalkenyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; CH3; OH; O-glycoside; C-glycoside; sulfated O-glycoside; sulfated C-glycoside; a chlorine; a CHO (aldehyde); a sulfate; an optionally substituted and/or optionally branched, C10 to C15 alkenyl; or an optionally substituted and/or optionally branched, C10 to C15 polyalkenyl.

R4 is CH3; OH; OCH3; a chlorine, or a 3,3-dimethylallyl chain (1h).

R5 is H; an optionally branched C1 to C20 alkyl; an optionally branched, C2 to C20 alkenyl; or an optionally branched, C4 to C20 polyalkenyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; CH3; OH; O-glycoside; C-glycoside; sulfated O-glycoside; sulfated C-glycoside; a chlorine; a CHO (aldehyde); a sulfate; an optionally substituted and/or optionally branched, C10 to C15 alkenyl; or an optionally substituted and/or optionally branched, C10 to C15 polyalkenyl.

R4 is H; CH3; OH; OCH3; a chlorine; or a 3,3-dimethylallyl chain (1h).

R5 is an optionally branched C1 to C20 alkyl; an optionally branched, C2 to C20 alkenyl; or an optionally branched, C4 to C20 polyalkenyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is CH3; OH; O-glycoside; C-glycoside; sulfated O-glycoside; sulfated C-glycoside; a chlorine; a CHO (aldehyde); a sulfate; or an optionally substituted and/or optionally branched, C10 to C15 alkenyl.

R4 is H; CH3; OH; OCH3; a chlorine, or a 3,3-dimethylallyl chain (1h).

R5 is H; an optionally branched C1 to C20 alkyl; an optionally branched, C2 to C20 alkenyl; or an optionally branched, C4 to C20 polyalkenyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; CH3; OH; O-glycoside; C-glycoside; sulfated O-glycoside; sulfated C-glycoside; a chlorine; a CHO (aldehyde); a sulfate; or an optionally substituted and/or optionally branched, C10 to C15 alkenyl.

R4 is CH3; OH; OCH3; a chlorine; or a 3,3-dimethylallyl chain (1h).

R5 is H; an optionally branched C1 to C20 alkyl; an optionally branched, C2 to C20 alkenyl; or an optionally branched, C4 to C20 polyalkenyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; CH3; OH; O-glycoside; C-glycoside; sulfated O-glycoside; sulfated C-glycoside; a chlorine; a CHO (aldehyde); a sulfate; or an optionally substituted and/or optionally branched, C10 to C15 alkenyl.

R4 is H; CH3; OH; OCH3; a chlorine; or a 3,3-dimethylallyl chain (1h).

R5 is an optionally branched C1 to C20 alkyl; an optionally branched, C2 to C20 alkenyl; or an optionally branched, C4 to C20 polyalkenyl, or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methyl-1-propen-1-yl)-3-furanyl]-2-hexen-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (1b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (1b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 3-hydroxy-3-methyl-1-butenyl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxo-pentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyl-octyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxo-pentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain exclusively represented by: 3,7,11-Trimethyldodecyl (hexahydrofarnesyl) (3a); a C20 isoprenoid chain exclusively represented by: 3,7,11,15-Tetramethylhexadecyl (phytanyl) (4a); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl) methyl (17c), 8-(3,4-dihydroxyphenyl)-4,7-octadien-1-yl (18a);

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain exclusively represented by: 3,7,11-Trimethyldodecyl (hexahydrofarnesyl) (3a); a C20 isoprenoid chain exclusively represented by: 3,7,11,15-Tetramethylhexadecyl (phytanyl) (4a); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl) methyl (17c), 8-(3,4-dihydroxyphenyl)-4,7-octadien-1-yl (18a);

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2, 6,10-dodecatrien-1-yl (farnesyl) (3b), 7-hydroxy-3,7, 11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain exclusively represented by: 3,7,11-Trimethyldodecyl (hexahydrofarnesyl) (3a); a C20 isoprenoid chain exclusively represented by: 3,7,11,15-Tetramethylhexadecyl (phytanyl) (4a); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl) methyl (17c), 8-(3,4-dihydroxyphenyl)-4,7-octadien-1-yl (18a);

R4 is H; OH; OCH3; O-glycoside; C-glycoside; acylated O-glycoside; acylated C-glycoside; sulfated O-glycoside; sulfated C-glycoside; a Cl, I, or F halogen atom;

a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (1b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: 8-pentadecen-1-yl (12e), 8-heptadecen-1-yl (12f), 10-heptadecen-1-yl (12g), 10-(acetyloxy)-8-pentadecenyl (13a), or a (substituted) polyalkenyl chain among the following representatives: 8,11-heptadecadien-1-yl (16a), 8-(3,4-dihydroxyphenyl)-4,7-octadien-1-yl (18a);

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloctyl (tetrahydrogeranyl) (2a), 3,7-dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: 8-pentadecen-1-yl (12e), 8-heptadecen-1-yl (12f), 10-heptadecen-1-yl (12g), 10-(acetyloxy)-8-pentadecenyl (13a), or a (substituted) polyalkenyl chain among the following representatives: 8,11-heptadecadien-1-yl (16a), 8-(3,4-dihydroxyphenyl)-4,7-octadien-1-yl (18a);

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloctyl (tetrahydrogeranyl) (2a), 3,7-dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: 8-pentadecen-1-yl (12e), 8-heptadecen-1-yl (12f), 10-heptadecen-1-yl (12g), 10-(acetyloxy)-8-pentadecenyl (13a), or a (substituted) polyalkenyl chain among the following representatives: 8,11-heptadecadien-1-yl (16a), 8-(3,4-dihydroxyphenyl)-4,7-octadien-1-yl (18a);

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloctyl (tetrahydrogeranyl) (2a), 3,7-dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 5-methyl-2-(1-methylethyl)cyclohexyl (2o); a C15 isoprenoid chain exclusively represented by: 3,7,11-Trimethyldodecyl (hexahydrofarnesyl) (3a); a C20 isoprenoid chain exclusively represented by: 3,7,11,15-Tetramethylhexadecyl (phytanyl) (4a); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), (tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); or a (substituted) alkenyl chain among the following representatives: 8-pentadecen-1-yl (12e), 8-heptadecen-1-yl (12f), 10-heptadecen-1-yl (12g), 10-(acetyloxy)-8-pentadecenyl (13a);

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloctyl (tetrahydrogeranyl) (2a), 3,7-dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 5-methyl-2-(1-methylethyl)cyclohexyl (2o); a C15 isoprenoid chain exclusively represented by: 3,7,11-Trimethyldodecyl (hexahydrofarnesyl) (3a); a C20 isoprenoid chain exclusively represented by: 3,7,11,15-Tetramethylhexadecyl (phytanyl) (4a); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl) ethyl (7b), (tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); or a (substituted) alkenyl chain among the following representatives: 8-pentadecen-1-yl (12e), 8-heptadecen-1-yl (12f), 10-heptadecen-1-yl (12g), 10-(acetyloxy)-8-pentadecenyl (13a);

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloctyl (tetrahydrogeranyl) (2a), 3,7-dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g); a C10 isoprenoid chain among the following representatives:

3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 5-methyl-2-(1-methylethyl)cyclohexyl (2o); a C15 isoprenoid chain exclusively represented by: 3,7,11-Trimethyldodecyl (hexahydrofarnesyl) (3a); a C20 isoprenoid chain exclusively represented by: 3,7,11,15-Tetramethylhexadecyl (phytanyl) (4a); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: 8-pentadecen-1-yl (12e), 8-heptadecen-1-yl (12f), 10-heptadecen-1-yl (12g), 10-(acetyloxy)-8-pentadecenyl (13a);

R4 is H; OH; $OCH_3$; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a primary, secondary, or tertiary amine; a primary or secondary amide; a cyano; a nitro; a sulfonate; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is OH; $OCH_3$; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a secondary, or tertiary amine; a primary or secondary amide; a cyano; a nitro; a sulfonate; a sulfate; a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloctyl (tetrahydrogeranyl) (2a), 3,7-dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2, 6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 and R5 are each independently H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain exclusively represented by: 3,7,11-Trimethyldodecyl (hexahydrofarnesyl) (3a); a C20 isoprenoid chain exclusively represented by: 3,7,11,15-Tetramethylhexadecyl (phytanyl) (4a); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (1b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain exclusively represented by: 3,7,11-Trimethyldodecyl (hexahydrofarnesyl) (3a); a C20 isoprenoid chain exclusively represented by: 3,7,11,15-Tetramethylhexadecyl (phytanyl) (4a); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl) methyl (17c), 8-(3,4-dihydroxyphenyl)-4,7-octadien-1-yl (18a);

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (1b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain exclusively represented by: 3,7,11-Trimethyldodecyl (hexahydrofarnesyl) (3a); a C20 isoprenoid chain exclusively represented by: 3,7,11,15-Tetramethylhexadecyl (phytanyl) (4a); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl) methyl (17c), 8-(3,4-dihydroxyphenyl)-4,7-octadien-1-yl (18a);

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives:

3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (1b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: 8-pentadecen-1-yl (12e), 8-heptadecen-1-yl (12f), 10-heptadecen-1-yl (12g), 10-(acetyloxy)-8-pentadecenyl (13a), or a (substituted) polyalkenyl chain among the following representatives: 8,11-heptadecadien-1-yl (16a), 8-(3,4-dihydroxyphenyl)-4,7-octadien-1-yl (18a);

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain exclusively represented by: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloctyl (tetrahydrogeranyl) (2a), 3,7-dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: 8-pentadecen-1-yl (12e), 8-heptadecen-1-yl (12f), 10-heptadecen-1-yl (12g), 10-(acetyloxy)-8-pentadecenyl (13a), or a (substituted) polyalkenyl chain among the following representatives: 8,11-heptadecadien-1-yl (16a), 8-(3,4-dihydroxyphenyl)-4,7-octadien-1-yl (18a);

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloctyl (tetrahydrogeranyl) (2a), 3,7-dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: 8-pentadecen-1-yl (12e), 8-heptadecen-1-yl (12f), 10-heptadecen-1-yl (12g), 10-(acetyloxy)-8-pentadecenyl (13a), or a (substituted) polyalkenyl chain among the following representatives: 8,11-heptadecadien-1-yl (16a), 8-(3,4-dihydroxyphenyl)-4,7-octadien-1-yl (18a);

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-

[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (1b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloctyl (tetrahydrogeranyl) (2a), 3,7-dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 5-methyl-2-(1-methylethyl)cyclohexyl (2o); a C15 isoprenoid chain exclusively represented by: 3,7,11-Trimethyldodecyl (hexahydrofarnesyl) (3a); a C20 isoprenoid chain exclusively represented by: 3,7,11,15-Tetramethylhexadecyl (phytanyl) (4a); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), (tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); or a (substituted) alkenyl chain among the following representatives: 8-pentadecen-1-yl (12e), 8-heptadecen-1-yl (12f), 10-heptadecen-1-yl (12g), 10-(acetyloxy)-8-pentadecenyl (13a);

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloctyl (tetrahydrogeranyl) (2a), 3,7-dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 5-methyl-2-(1-methylethyl)cyclohexyl (2o); a C15 isoprenoid chain exclusively represented by: 3,7,11-Trimethyldodecyl (hexahydrofarnesyl) (3a); a C20 isoprenoid chain exclusively represented by: 3,7,11,15-Tetramethylhexadecyl (phytanyl) (4a); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylethyl (7a), 2-hydroxy-2-(2-hydroxyphenyl) ethyl (7b), (tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); or a (substituted) alkenyl chain among the following representatives: 8-pentadecen-1-yl (12e), 8-heptadecen-1-yl (12f), 10-heptadecen-1-yl (12g), 10-(acetyloxy)-8-pentadecenyl (13a);

R4 is OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b);

a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloctyl (tetrahydrogeranyl) (2a), 3,7-dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 5-methyl-2-(1-methylethyl)cyclohexyl (2o); a C15 isoprenoid chain exclusively represented by: 3,7,11-Trimethyldodecyl (hexahydrofarnesyl) (3a); a C20 isoprenoid chain exclusively represented by: 3,7,11,15-Tetramethylhexadecyl (phytanyl) (4a); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl) ethyl (7b), (tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); or a (substituted) alkenyl chain among the following representatives: 8-pentadecen-1-yl (12e), 8-heptadecen-1-yl (12f), 10-heptadecen-1-yl (12g), 10-(acetyloxy)-8-pentadecenyl (13a);

R4 is H; OH; OCH3; O-glycoside; C-glycoside; acylated O-glycoside; acylated C-glycoside; sulfated O-glycoside; sulfated C-glycoside; a Cl, I, or F halogen atom; a primary, secondary, or tertiary alcohol; a ketone; an aldehyde; an ester; a sulfate; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a);

R5 is OH; OCH3; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; an ester; a sulfate; a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloctyl (tetrahydrogeranyl) (2a), 3,7-dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b); a C20 isoprenoid chain among the following representatives: 3,7,11,15-Tetramethylhexadecyl (phytanyl) (4a), (2E,6E,10E)-3,7,11,15-tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is CH3, OH; O-glycoside; C-glycoside; sulfated O-glycoside; sulfated C-glycoside; a chlorine; a CHO (aldehyde); a sulfate; a C5 isoprenoid chain among the following representatives: 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methyl-1-propen-1-yl)-3-furanyl]-2-hexen-1-yl (3d); or a (substituted) polyalkenyl chain exclusively represented by: 8-(3,4-dihydroxyphenyl)-4,7-octadien-1-yl (18a);

R4 is H; CH3, OH; OCH3; a chlorine, or a 3,3-dimethylallyl chain (1h);

R5 is H; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is H; CH3, OH; O-glycoside; C-glycoside; sulfated O-glycoside; sulfated C-glycoside; a chlorine; a CHO (aldehyde); a sulfate; a C5 isoprenoid chain among the following representatives: 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methyl-1-propen-1-yl)-3-furanyl]-2-hexen-1-yl (3d); or a (substituted) polyalkenyl chain exclusively represented by: 8-(3,4-dihydroxyphenyl)-4,7-octadien-1-yl (18a);

R4 is CH3, OH; OCH3; a chlorine; or a 3,3-demethylallyl chain (1h);

R5 is H; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 3-hydroxy-3-methyl-1-butenyl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; CH3, OH; O-glycoside; C-glycoside; sulfated O-glycoside; sulfated C-glycoside; a chlorine; a CHO (aldehyde); a sulfate; a C5 isoprenoid chain among the following representatives: 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 3-hydroxy-3-methyl-1-butenyl (1n), 2-hydroxy-3-methyl-3-buten-1-yl (1o), 3-methyl-1,3-butadienyl (1p); a C10 isoprenoid chain among the following representatives: 3,7-Dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methyl-1-propen-1-yl)-3-furanyl]-2-hexen-1-yl (3d); or a (substituted) polyalkenyl chain exclusively represented by: 8-(3,4-dihydroxyphenyl)-4,7-octadien-1-yl (18a);

R4 is H; CH3, OH; OCH3; a chlorine; or a 3,3-dimethylallyl chain (1h);

R5 is a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is CH3, OH; O-glycoside; C-glycoside; sulfated O-glycoside; sulfated C-glycoside; a chlorine; a CHO (aldehyde); a sulfate; a C5 isoprenoid chain among the following representatives: 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); or a C10 isoprenoid chain among the following representatives: 3,7-Dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o);

R4 is H; CH3, OH; OCH3; a chlorine; or a 3,3-dimethylallyl chain (1h);

R5 is H; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methyl-1-propen-1-yl)-3-furanyl]-2-hexen-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), (tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a).

or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; CH3; OH; O-glycoside; C-glycoside; sulfated O-glycoside; sulfated C-glycoside; a chlorine; a CHO (aldehyde); a sulfate; a C5 isoprenoid chain among the following representatives: 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); or a C10 isoprenoid chain among the following representatives: 3,7-Dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o);

R4 is CH3; OH; OCH3; a chlorine; or a 3,3-dimethylallyl chain (1h);

R5 is H; a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl) methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; CH3; OH; O-glycoside; C-glycoside; sulfated O-glycoside; sulfated C-glycoside; a chlorine; a CHO (aldehyde); a sulfate; a C5 isoprenoid chain among the following representatives: 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); or a C10 isoprenoid chain among the following representatives: 3,7-Dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o);

R4 is H; CH3; OH; a chlorine; or a 3,3-demethylallyl chain (1h);

R5 is a C5 isoprenoid chain among the following representatives: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p); a C10 isoprenoid chain among the following representatives: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl)furan-3-yl]hex-2-en-1-yl (3d); a C20 isoprenoid chain among the following representatives: 3,7,11,15-Tetramethylhexadecyl (phytanyl) (4a), (2E,6E,10E)-3,7,11,15-tetramethyl-hexadeca-2,6,10,14-tetraen-1-yl (geranylgeranyl) (4b); a (substituted) alkyl chain among the following representatives: Methyl, ethyl, propyl, butyl, pentyl, heptyl, nonyl undecyl, pentadecyl, heptadecyl, eicosyl, hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p), benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e), 2-hydroxy-2-phenylyethyl (7a), 2-hydroxy-2-(2-hydroxyphenyl)ethyl (7b), tetrahydro-6-methyl-2H-pyran-2-yl)methyl (8a), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 1-hydroxy-2-oxopropyl (10a), 13-hydroxy-2-oxotridecyl (10b), 2-(4-hydroxyphenyl)-2-oxoethyl (11a), 2-oxo-2-phenylethyl (11b); a (substituted) alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g), 10-(acetyloxy)-8-pentadecenyl (13a), 2-phenylethenyl (14a), 1-hydroxymethylene-2-oxopropyl (15a); or a (substituted) polyalkenyl chain among the following representatives: 8,11-heptadecadien-1-yl (16a), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c), 8-(3,4-dihydroxyphenyl)-4,7-octadien-1-yl (18a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is CH3; OH; O-glycoside; C-glycoside; sulfated O-glycoside; sulfated C-glycoside; a chlorine; a CHO (aldehyde); a sulfate; a C10 isoprenoid chain among the following representatives: 3,7-Dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: (2E,6E)-3,7,11-Trimethyl-2,6,10-dodecatrien-1-yl (farnesyl) (3b), 7-hydroxy-3,7,11-trimethyl-2,10-dodecadien-1-yl (3c), 3-methyl-6-[5-(2-methyl-1-propen-1-yl)-3-furanyl]-2-hexen-1-yl (3d); or a (substituted) polyalkenyl chain exclusively represented by: 8-(3,4-dihydroxyphenyl)-4,7-octadien-1-yl (18a);

R4 is H; CH3; OH; OCH3; a chlorine; or a 3,3-dimethylallyl chain (1h);

R5 is H; a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j); a C15 isoprenoid chain, exclusively represented by: (2E,6E)-3,7,11-Trimethyl-2,6,10-dodecatrien-1-yl (farnesyl) (3b); a C20 isoprenoid chain, exclusively represented by: (2E,6E,10E)-3,7,11,15-Tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain, exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; CH3; OH; O-glycoside; C-glycoside; sulfated O-glycoside; sulfated C-glycoside; a chlorine; a CHO (aldehyde); a sulfate; a C10 isoprenoid chain among the following representatives: 3,7-Dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl) cyclohexyl (2o); a C15 isoprenoid chain among the following representatives: (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methyl-1-propen-1-yl)-3-furanyl]-2-hexen-1-yl (3d); or a (substituted) polyalkenyl chain exclusively represented by: 8-(3,4-dihydroxyphenyl)-4,7-octadien-1-yl (18a);

R4 is CH3; OH; OCH3; a chlorine, or a 3,3-dimethylallyl chain (1h);

R5 is H; C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j); a C15 isoprenoid chain, exclusively represented by: (2E,6E)-3,7,11-Trimethyl-2,6,10-dodecatrien-1-yl (farnesyl) (3b); a C20 isoprenoid chain, exclusively represented by: (2E,6E,10E)-3,7,11,15-Tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain, exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate; R2 is H; CH3; OH; O-glycoside; C-glycoside; sulfated O-glycoside; sulfated C-glycoside; a chlorine; a CHO (aldehyde); a sulfate; a C10 isoprenoid chain among the following representatives: 3,7-Dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl] methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o); a C15 isoprenoid chain among the following representatives: (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methyl-1-propen-1-yl)-3-furanyl]-2-hexen-1-yl (3d); or a (substituted) polyalkenyl chain exclusively represented by: 8-(3,4-dihydroxyphenyl)-4,7-octadien-1-yl (18a);

R4 is H; CH3; OH; OCH3; a chlorine; or a 3,3-dimethylallyl chain (1h);

R5 is C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j); a C15 isoprenoid chain, exclusively represented by: (2E,6E)-3,7,11-Trimethyl-2,6,10-dodecatrien-1-yl (farnesyl) (3b); a C20 isoprenoid chain, exclusively represented by: (2E,6E,10E)-3,7,11,15-Tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain, exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate.

R2 is CH3, OH; O-glycoside; C-glycoside; sulfated O-glycoside; sulfated C-glycoside; a chlorine; a CHO (aldehyde); a sulfate; or a C10 isoprenoid chain among the following representatives: 3,7-Dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 5-methyl-2-(1-methylethyl)cyclohexyl (2o);

R4 is H; CH3; OH; OCH3; a chlorine, or a 3,3-dimethylallyl chain (1h).

R5 is H; a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j); a C15 isoprenoid chain, exclusively represented by: (2E,6E)-3,7,11-Trimethyl-2,6,10-dodecatrien-1-yl (farnesyl) (3b); a C20 isoprenoid chain, exclusively represented by: (2E,6E,10E)-3,7,11,15-Tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain, exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; CH3, OH; O-glycoside; C-glycoside; sulfated O-glycoside; sulfated C-glycoside; a chlorine; a CHO (aldehyde); a sulfate; or a C10 isoprenoid chain among the following representatives: 3,7-Dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 5-methyl-2-(1-methylethyl)cyclohexyl (2o);

R4 is CH3; OH; OCH3; a chlorine; or a 3,3-dimethylallyl chain (1h).

R5 is H; a C5 isoprenoid chain among the following representatives: 3-Methylbutyl (1a), 3-methyl-2-buten- 1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j); a C15 isoprenoid chain, exclusively represented by: (2E,6E)-3,7,11-Trimethyl-2,6,10-dodecatrien-1-yl (farnesyl) (3b); a C20 isoprenoid chain, exclusively represented by: (2E,6E,10E)-3,7,11,15-Tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain, exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-aliphatic saturated or unsaturated acyl, O-glycoside; acylated O-glycoside; sulfated O-glycoside; or a sulfate;

R2 is H; CH3, OH; O-glycoside; C-glycoside; sulfated O-glycoside; sulfated C-glycoside; a chlorine; a CHO (aldehyde); a sulfate; or a C10 isoprenoid chain among the following representatives: 3,7-Dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 5-methyl-2-(1-methylethyl)cyclohexyl (2o);

R4 is H; CH3; OH; OCH3; a chlorine; or a 3,3-dimethylallyl chain (1h).

R5 is a C5 isoprenoid chain among the following representatives: 3-Methylbutyl (1a), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3-methyl-1,3-butadienyl (1p); a C10 isoprenoid chain among the following representatives: 3,7-Dimethyloct-6-en-1-yl (citronellyl) (2c), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j); a C15 isoprenoid chain, exclusively represented by: (2E,6E)-3,7,11-Trimethyl-2,6,10-dodecatrien-1-yl (farnesyl) (3b); a C20 isoprenoid chain, exclusively represented by: (2E,6E,10E)-3,7,11,15-Tetramethylhexadeca-2,6,10,14-tetraen-1-yl (geranylgeranyl) (4b); a linear or branched alkyl chain among the following representatives: Methyl, ethyl, propyl, butyl, pentyl, heptyl, nonyl undecyl, pentadecyl, heptadecyl, eicosyl; an alkenyl chain among the following representatives: ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g); or a polyalkenyl chain, exclusively represented by: 8,11-heptadecadien-1-yl (16a), or a derivative or analogue thereof, for use in the activation of AMPK.

In some embodiments, a OCH3 group can cyclize with a neighboring OH group to form a methylene dioxy bridge.

In one embodiment, R1 and R3 are each independently OH; OCH3; O-glycoside; or a sulfate;

R2 is H; 3-methyl-2-buten-1-yl (3,3-dimethylallyl) (1h); or (2E)-3,7-dimethyl-2,6-octadien-1-yl (geranyl) (2h);

R4 is H.

R5 is pentyl; benzyl (6a); 2-phenethyl (6b); or phenylethenyl (14a), or a derivative or analogue thereof, for use in the activation of AMPK.

In one embodiment, R1=OH; O-glycoside; or a sulfate;

R2 is H; [3-methyl-3-(4-methyl-3-penten-1-yl)-2-oxiranyl]methyl (geranyl 2,3-epoxide) (2e); 3-methyl-6-(1-methylethenyl)-2-cyclohexen-1-yl (2g); (2E)-3,7-dimethyl-2,6-octadien-1-yl (geranyl) (2h); (2Z)-3,7-dimethyl-2,6-octadien-1-yl (neryl) (2i); or 5-methyl-2-(1-methylethyl)cyclohexyl (2o);

R3 is OH; OCH3; O-glycoside; or a sulfate;

R4 is H;

R5 is CH3; n-propyl, n-butyl, or pentyl, or a derivative or analogue thereof, for use in the activation of AMPK.

In one preferred embodiment, said compound is compound 1, CAS number 1244-58-2 Cannabidiolic acid.

Other names for cannabidiolic acid include:

Benzoic acid, 2,4-dihydroxy-3-[(1R,6R)-3-methyl-6-(1-methylethenyl)-2-cyclohexen-1-yl]-6-pentyl- Benzoic acid, 2,4-dihydroxy-3-[3-methyl-6-(1-methylethenyl)-2-cyclohexen-1-yl]-6-pentyl-, (1R-trans)-

β-Resorcylic acid, 3-p-mentha-1,8-dien-3-yl-6-pentyl- 2,4-Dihydroxy-3-[(1R,6R)-3-methyl-6-(1-methylethenyl)-2-cyclohexen-1-yl]-6-pentylbenzoic acid

CBDA

Cannabidiol acid

Cannabidiolcarboxylic acid

Cannabinoid CBDA

Compound 1

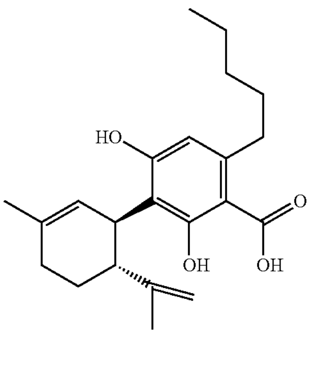

Definitions

General Chemistry Terminology

The descriptions of simple chains like methyl, pentyl, dodecyl are known to the person skilled in the art. For example, methyl is an alkyl derived from methane, containing one carbon atom bonded to three hydrogen atoms—CH3 chemical formula —C3H. Pentyl is a five-carbon alkyl functional group (substituent) with chemical formula —C5H11. Dodecyl is a twelve-carbon alkyl functional group (substituent) with chemical formula —C12H25.

For the avoidance of doubt, more complex chains have been drawn and a number attributed as a quick reference.

In all structures, the dot represents the point of insertion of the chain on the aromatic ring. For example, if in Markush structure A, R2 is 3-methyl-2-buten-1-yl (1h), this corresponds to structure B:

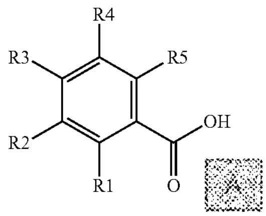

A

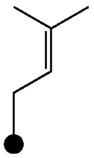

1 h

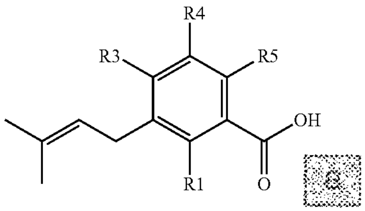

B

The term C5 isoprenoid unit refers to the following substituents: 3-Methylbutyl (1a), 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 3-methyl-2-oxobutyl (1g), 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 3-methyl-1,3-butadienyl (1p).

1a

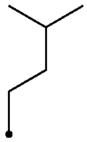

1b

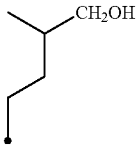

1c

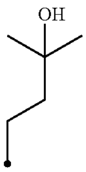

1d

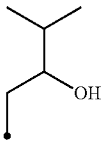

-continued

1e

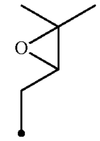

1f

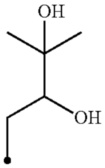

1g

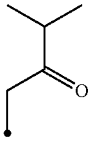

1h

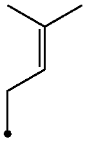

1i

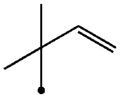

1j

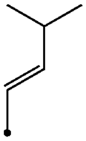

1k

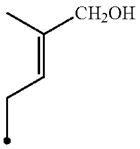

1l

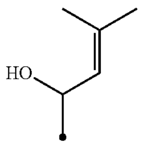

1m

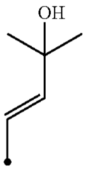

1n

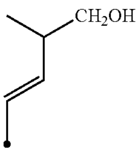

-continued

1o

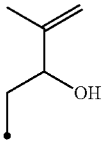

1p

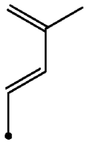

The term C10 isoprenoid unit refers to the following substituents: 3,7-Dimethyloctyl (tetrahydrogeranyl) (2a), 8-hydroxy-3,7-dimethyloctyl (2b), 3,7-dimethyloct-6-en-1-yl (citronellyl) (2c), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 3,7-dimethyl-5-oxo-2,6-octadienyl (2n), 5-methyl-2-(1-methylethyl)cyclohexyl (2o).

2a

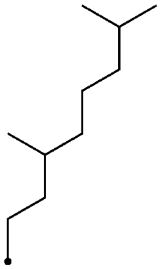

2b

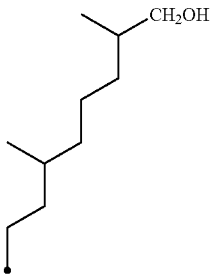

2c

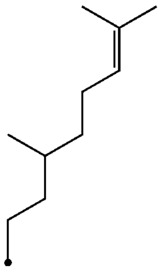

-continued
2d
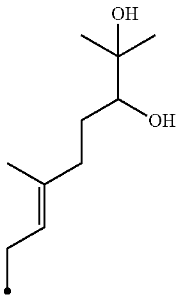
2e
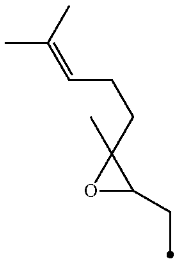
2f
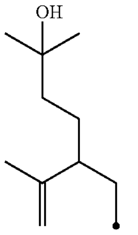
2g
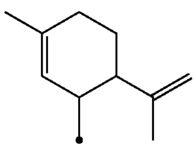
2h
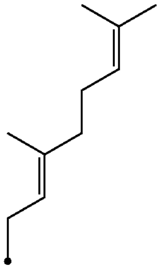
2i
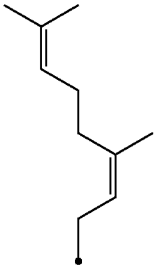
-continued
2j
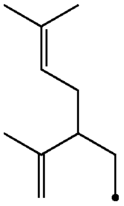
2k
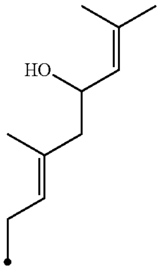
2l
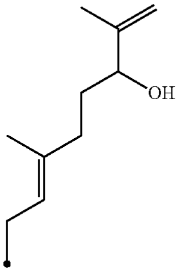
2m
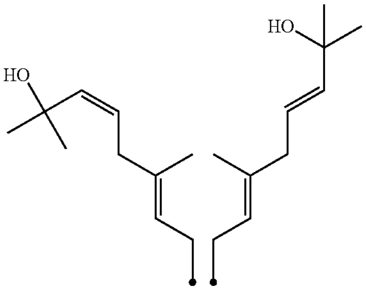
2n
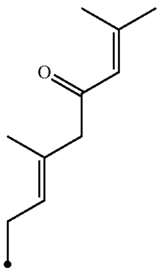
2o
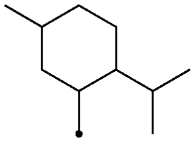
The term C15 isoprenoid unit refers to the following substituents: 3,7,11-Trimethyldodecyl (hexahydrofarnesyl) (3a), (2E,6E)-3,7,11-trimethyl-2,6,10-dodecatrien-1-yl (farnesyl) (3b), 7-hydroxy-3,7,11-trimethyl-2,10-dodecadien-1-yl (3c), 3-methyl-6-[5-(2-methylprop-1-en-1-yl) furan-3-yl]hex-2-en-1-yl (3d).
3a
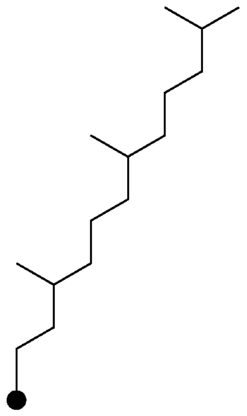
3b
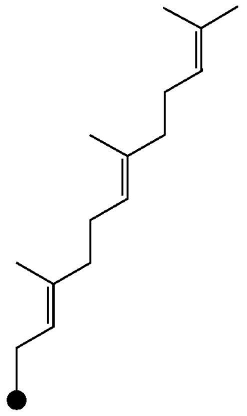
3c
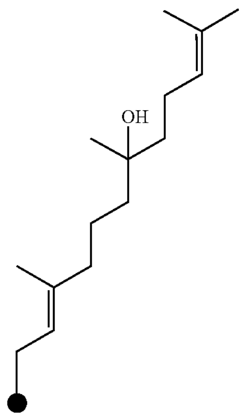
-continued
3d
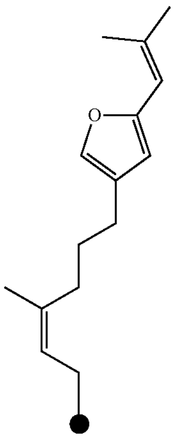
C20 isoprenoid unit refers to the following substituents: 3,7,11,15-Tetramethylhexadecyl (phytanyl) (4a), (2E,6E, 10E)-3,7,11,15-tetramethylhexadeca-2,6,10,14-tetraen-1-yl (geranylgeranyl) (4b).
4a
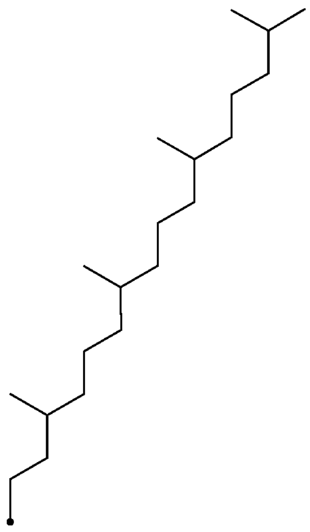
4b
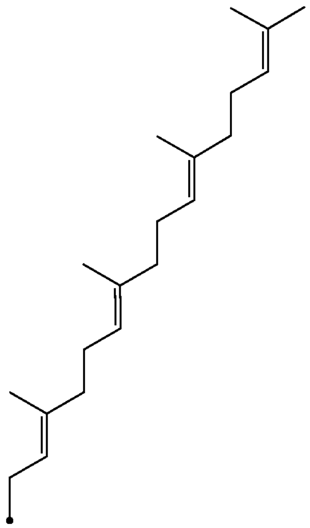

The term "alkyl" refers to a branched or unbranched saturated hydrocarbon chain having from 1 to 20 carbon atoms, or from 1 to 15 carbon atoms, or from 1 to 10 carbon atoms, or from 1 to 7 carbon atoms, or from 1 to 5 carbon atoms, or from 1 to 3 carbon atoms. The alkyl chain may be cyclic, in which case it would be known as "cycloalkyl" group.

Non-limiting examples of branched or unbranched alkyl chains include: methyl, ethyl, n-propyl, iso-propyl, n-butyl, iso-butyl, t-butyl, pentyl, hexyl, heptyl, nonyl, decyl, undecyl, tetradecyl, pentadecyl, heptadecyl, eicosyl.

A non-limiting example of cycloalkyl chain includes: 5-methyl-2-(1-methylethyl)cyclohexyl (2o)

The term "substituted alkyl" refers to:

1) an alkyl chain as defined above, having 1, 2, 3, 4 or 5 substituents, (in some embodiments, 1, 2 or 3 substituents) selected from the group consisting of alkyl; alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)— cycloalkyl, —S(O)-heterocyclyl, —S(O)-aryl, —S(O)-heteroaryl, —S(O)2-alkyl, —S(O)2-cycloalkyl, —S(O)2-heterocyclyl, —S(O)2-aryl and —S(O)2-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, and —S(O)n R<a>, in which R<a> is alkyl, aryl or heteroaryl and n is 0, 1 or 2;

One of the oxygen substituents of the alkyl chain can be joined by single bonds to two adjacent carbon atoms of the same alkyl chain, to form an epoxy group, i.e. a three-membered epoxide ring.

Non limiting examples of alkyl chains substituted by hydroxy, alkoxy, and/or acyloxy groups, or containing an epoxy group include: 4-hydroxy-3-methylbutyl (1b), 3-hydroxy-3-methylbutyl (1c), 2-hydroxy-3-methylbutyl (1d), (3,3-dimethyl-2-oxiranyl)methyl (epoxyprenyl) (1e), 2,3-dihydroxy-3-methylbutyl (1f), 8-hydroxy-3,7-dimethyloctyl (2b), hydroxymethyl (5a), 6-hydroxyheptyl (5b), 8-hydroxynonyl (5c), 12-hydroxytridecyl (5d), 2-hydroxytridecyl (5e), 2,12-dihydroxytridecyl (5f), 2-hydroxypentadecyl (5g), 14-hydroxypentadecyl (5h), 16-hydroxyheptadecyl (5i), 10-methoxyundecyl (5j), 12-methoxytridecyl (5k), 2-(acetyloxy)pentadecyl (5l), 2-(acetyloxy)-13-hydroxytridecyl (5m), 2-(acetyloxy)-12-hydroxytridecyl (5n), 2,12-bis(acetyloxy)tridecyl (5o), 2-(acetyloxy)tridecyl (5p).

5a

-continued

5b

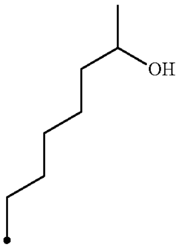

5c

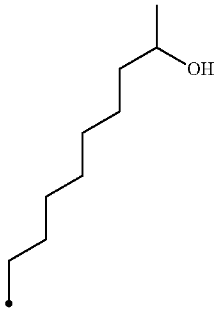

5d

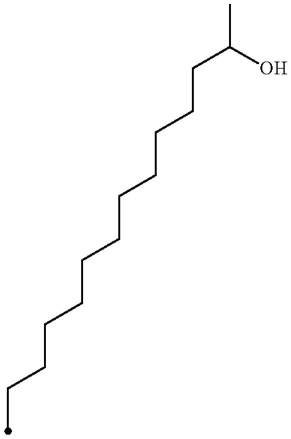

5e

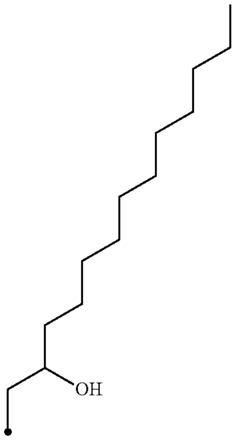

-continued
5f
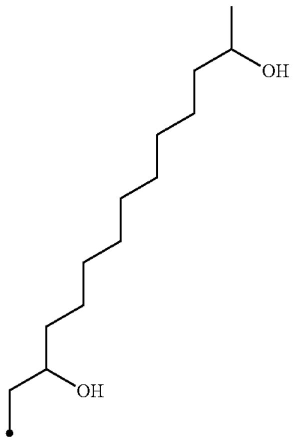
5g
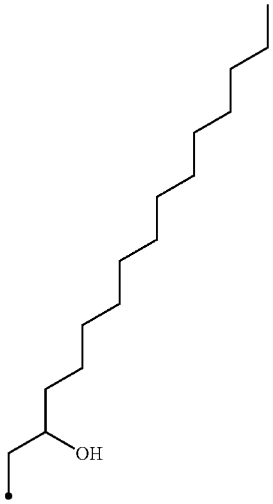
5h
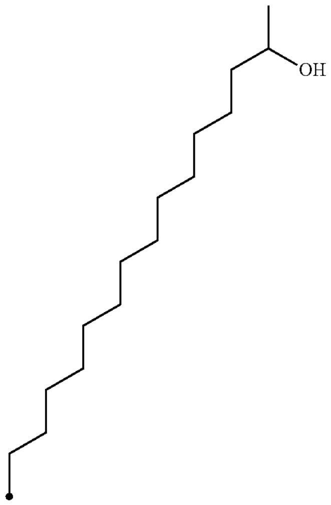
-continued
5i
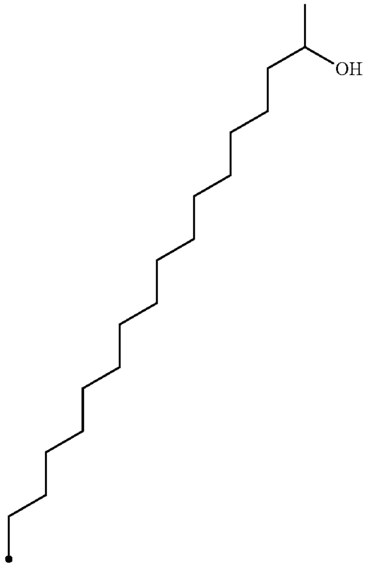
5j
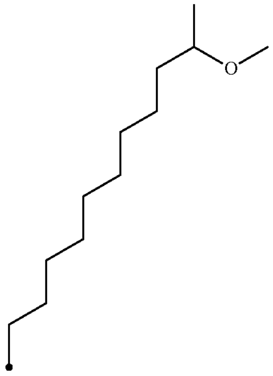
5k
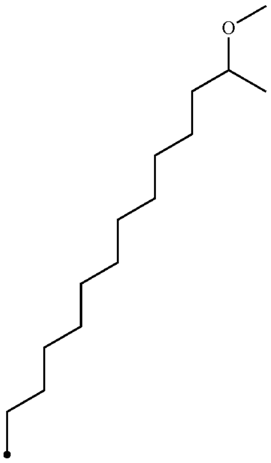

-continued
5l
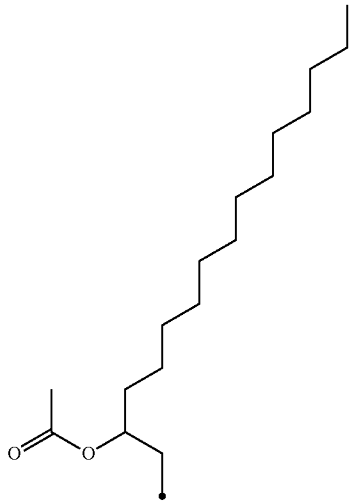
5m
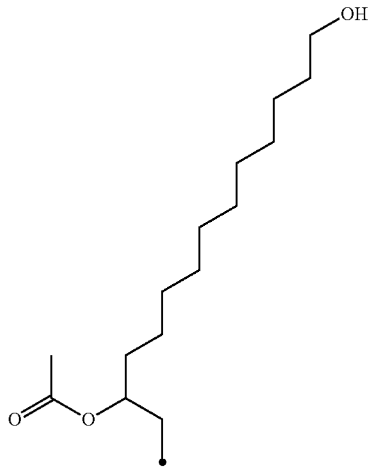
5n
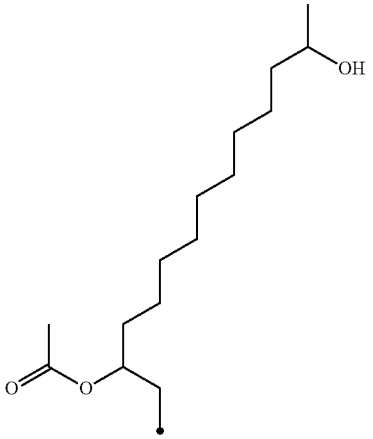
-continued
5o
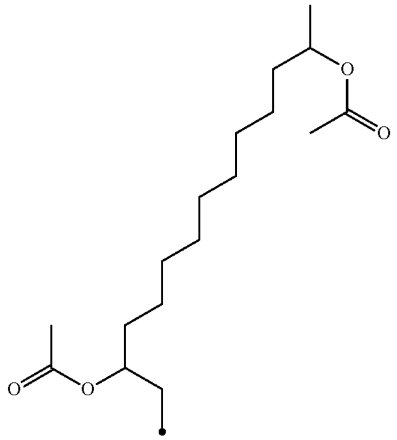
5p
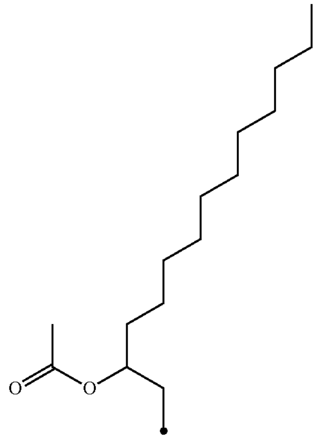
Non limiting examples of alkyl chains substituted by aryl/aryloxy groups include: Benzyl (6a), 2-phenylethyl (6b), 2-(4-hydroxyphenyl)ethyl (6c), 2-(3,4-dihydroxyphenyl)ethyl (6d), 2-(4-methoxyphenyl)ethyl (6e).
6a
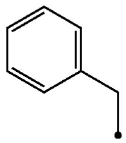
6b
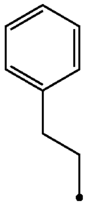

-continued

6c

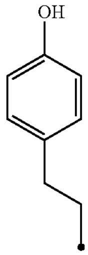

6d

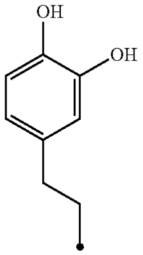

6e

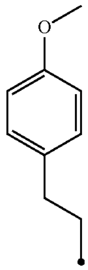

Non limiting examples of alkyl chains substituted by aryl/aryloxy and hydroxy groups include: 2-Hydroxy-2-phenylyethyl (7a), 2-hydroxy-2-(2-hydroxyphenyl)ethyl (7b).

7a

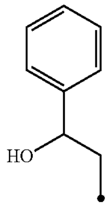

7b

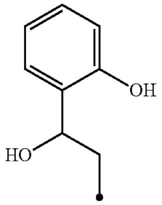

A non-limiting example of alkyl chain substituted by a heterocyclyl group includes: Tetrahydro-6-methyl-2H-pyran-2-yl)methyl (8a).

8a

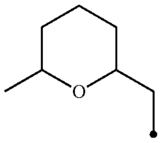

or 2) an alkyl chain as defined above that is interrupted by 1-5 atoms (e.g. 1, 2, 3, 4 or 5 atoms) independently chosen from oxygen, sulfur and NR<a>, where R<a> is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, and —S(O)n R<a>, in which R<a> is alkyl, aryl or heteroaryl and n is 0, 1 or 2;

or 3) an alkyl chain as defined above that has both 1, 2, 3, 4 or 5 substituents as defined above and is also interrupted by 1-5 atoms (e.g. 1, 2, 3, 4 or 5 atoms) as defined above;

or 4) an alkyl chain as defined above in which one or more of the methylene group is replaced by a carbonyl group to give an oxo group.

Non limiting examples of alkyl chain in which one or more of the methylene group is replaced by a carbonyl group include: 3-methyl-2-oxobutyl (1g), 1,2-dioxopropyl (9a), 3-oxopentyl (9b), 2-oxopentyl (9c), 2-oxoheptyl (9d), 2-oxononyl (9e), 14-oxopentadecyl (9f), 2-oxotridecyl (9g), 2-oxotridecyl (9g).

9a

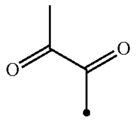

9b

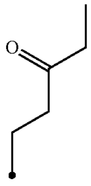

9c

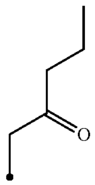

-continued

9d

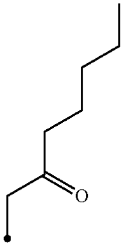

9e

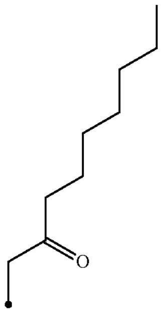

9f

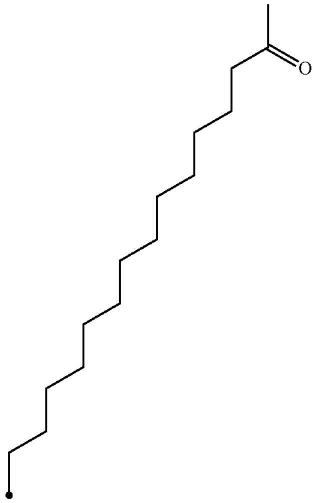

9g

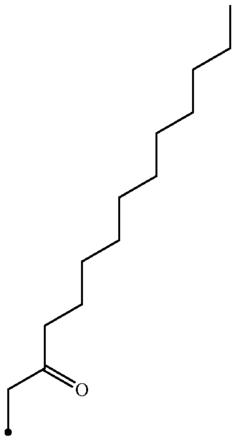

or 5) an alkyl chain as defined above in which one of the methylene group is replaced by a carbonyl group to give an oxo group, and has 1, 2, 3, 4 or 5 substituents as defined above, or is interrupted by 1-5 atoms (e.g. 1, 2, 3, 4 or 5 atoms) as defined above or has both 1, 2, 3, 4 or 5 substituents as defined above and is also interrupted by 1-5 atoms (e.g. 1, 2, 3, 4 or 5 atoms) as defined above.

Non limiting examples of alkyl chain in which one of the methylene group is replaced by a carbonyl group to give an oxo group, and has a hydroxy substituent include: 1-hydroxy-2-oxopropyl (10a), 13-hydroxy-2-oxotridecyl (10b).

10a

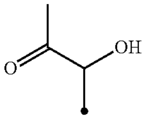

10b

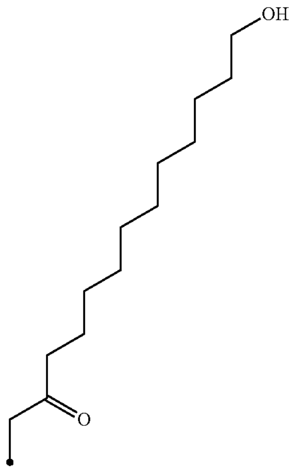

Non limiting examples of alkyl chains substituted by aryl/aryloxy, in which one of the methylene group is replaced by a carbonyl group to give an oxo group includes: 2-(4-hydroxyphenyl)-2-oxoethyl (11a), 2-oxo-2-phenylethyl (11b).

11a

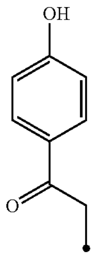

11b

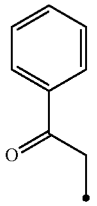

The term "alkenyl" refers to a type of alkyl chain as defined above, in which two atoms of the alkyl chain form a double bond that is not part of an aromatic group. That is, an alkenyl chain contains the pattern R—C(R)═C(R)—R, In one embodiment, R refers to the remaining portions of the alkenyl chain, which may be the same or different. The alkenyl moiety may be branched, straight chain, or cyclic (in which case, it would also be known as a "cycloalkenyl" group).

The term "substituted alkenyl" refers to:

1) an alkenyl chain as defined above, having 1, 2, 3, 4 or 5 substituents, (in some embodiments, 1, 2 or 3 substituents) selected from the group consisting of alkyl; alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)— cycloalkyl, —S(O)-heterocyclyl, —S(O)-aryl, —S(O)-heteroaryl, —S(O)2-alkyl, —S(O)2-cycloalkyl, —S(O)2-heterocyclyl, —S(O)2-aryl and —S(O)2-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, and —S(O)n R<a>, in which R<a> is alkyl, aryl or heteroaryl and n is 0, 1 or 2;

One of the oxygen substituents of the alkenyl chain can be joined by single bonds to two adjacent carbon atoms of the same alkenyl chain, to form an epoxy group, i.e. a three-membered epoxide ring.

or 2) an alkenyl chain as defined above that is interrupted by 1-5 atoms (e.g. 1, 2, 3, 4 or 5 atoms) independently chosen from oxygen, sulfur and NR<a>, where R<a> is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, and —S(O)n R<a>, in which R<a> is alkyl, aryl or heteroaryl and n is 0, 1 or 2;

or 3) an alkenyl chain as defined above that has both 1, 2, 3, 4 or 5 substituents as defined above and is also interrupted by 1-5 atoms (e.g. 1, 2, 3, 4 or 5 atoms) as defined above;

or 4) an alkenyl chain as defined above in which one or more of the methylene group is replaced by a carbonyl group to give an oxo group.

or 5) an alkenyl chain as defined above in which one of the methylene group is replaced by a carbonyl group to give an oxo group, and has 1, 2, 3, 4 or 5 substituents as defined above, or is interrupted by 1-5 atoms (e.g. 1, 2, 3, 4 or 5 atoms) as defined above or has both 1, 2, 3, 4 or 5 substituents as defined above and is also interrupted by 1-5 atoms (e.g. 1, 2, 3, 4 or 5 atoms) as defined above.

Non-limiting examples of alkenyl chains include: 3-methyl-2-buten-1-yl (3,3-dimethylallyl) (1h), 1,1-dimethyl-2-propen-1-yl (1,1-dimethylallyl) (1i), 3-methyl-1-buten-1-yl (1j), 3,7-dimethyloct-6-en-1-yl (citronellyl) (2c), ethenyl (12a), 1-propenyl (12b), 1-methylethenyl (12c), 1-methyl-1-propen-1-yl (12d), 8-pentadecen-1-yl (12e), 8-heptadecen-1-yl (12f), 10-heptadecen-1-yl (12g).

12a

12b

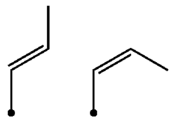

12c

12d

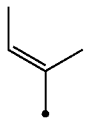

12e

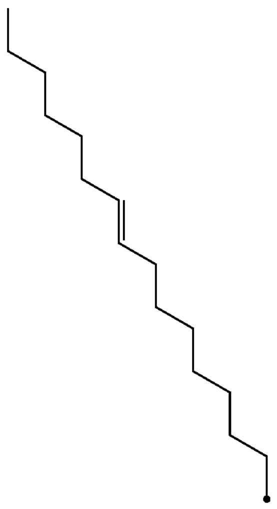

12f

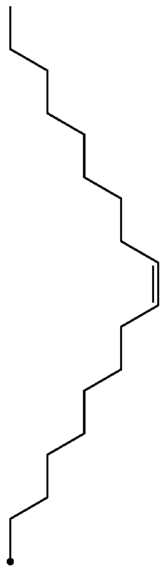

-continued

12g

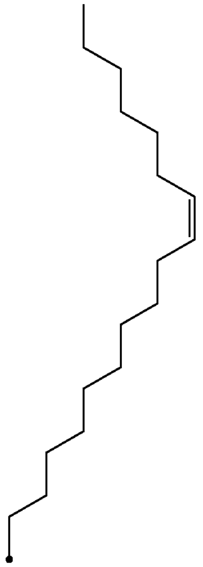

Non limiting examples of alkenyl chains substituted by hydroxy, and/or acyloxy groups, or containing an epoxy group include: 4-hydroxy-3-methyl-2-buten-1-yl (1k), 1-hydroxy-3-methyl-2-buten-1-yl (1l), 3-hydroxy-3-methyl-1-butenyl (1m), 4-hydroxy-3-methylbut-1-en-1-yl (1n), 2-hydroxy-3-methyl-3-buten-1-yl (1o), 6,7-dihydroxy-3,7-dimethyl-octa-2-enyl (2d), [3-methyl-3-(4-methyl-3-penten-1-yl)-2-oxiranyl]methyl (geranyl 2,3-epoxide) (2e), 5-hydroxy-5-methyl-2-(1-methylethenyl)hexyl (2f), 10-(acetyloxy)-8-pentadecenyl (13a).

13a

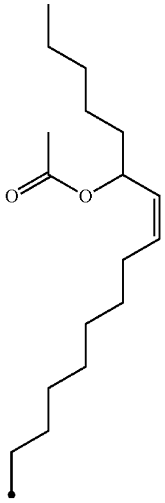

A non-limiting example of alkenyl chain substituted by an aryl group includes: 2-phenylethenyl (14a).

14a

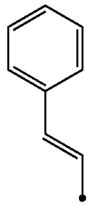

A non-limiting example of an alkenyl chain where one of the methylene is replaced by an oxo group includes: 1-hydroxymethylene-2-oxopropyl (15a).

15a

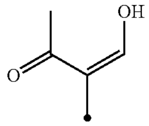

The term "alkynyl" refers to a type of alkyl chain as defined above in which two atoms of the alkyl chain form a triple bond. That is, an alkynyl chain contains the pattern R—C≡C—R, In one embodiment, R refers to the remaining portions of the alkynyl chain, which may be the same or different. Non-limiting examples of an alkynyl chain include —C≡CH, —C≡C—CH3 and —C ≡C—CH2-CH3. The "R" portion of the alkynyl moiety may be branched, straight chain, or cyclic. Alkynyl chains can be optionally substituted.

The term "substituted alkynyl" refers to:

1) an alkynyl chain as defined above, having 1, 2, 3, 4 or 5 substituents, (in some embodiments, 1, 2 or 3 substituents) selected from the group consisting of alkyl; alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)— cycloalkyl, —S(O)-heterocyclyl, —S(O)-aryl, —S(O)-heteroaryl, —S(O)2-alkyl, —S(O)2-cycloalkyl, —S(O)2-heterocyclyl, —S(O)2-aryl and —S(O)2-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, and —S(O)n R<a>, in which R<a> is alkyl, aryl or heteroaryl and n is 0, 1 or 2;

One of the oxygen substituents of the alkynyl chain can be joined by single bonds to two adjacent carbon atoms of the same alkynyl chain, to form an epoxy group, i.e. a three-membered epoxide ring.

or 2) an alkynyl chain as defined above that is interrupted by 1-5 atoms (e.g. 1, 2, 3, 4 or 5 atoms) independently chosen from oxygen, sulfur and NR<a>, where R<a> is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, and —S(O)n R<a>, in which R<a> is alkyl, aryl or heteroaryl and n is 0, 1 or 2;

or 3) an alkynyl chain as defined above that has both 1, 2, 3, 4 or 5 substituents as defined above and is also interrupted by 1-5 atoms (e.g. 1, 2, 3, 4 or 5 atoms) as defined above;

or 4) an alkynyl chain as defined above in which one or more of the methylene group is replaced by a carbonyl group to give an oxo group.

or 5) an alkynyl chain as defined above in which one of the methylene group is replaced by a carbonyl group to give an oxo group, and has 1, 2, 3, 4 or 5 substituents as defined above, or is interrupted by 1-5 atoms (e.g. 1, 2, 3, 4 or 5 atoms) as defined above or has both 1, 2, 3, 4 or 5 substituents as defined above and is also interrupted by 1-5 atoms (e.g. 1, 2, 3, 4 or 5 atoms) as defined above.

The term polyalkenyl refers to a chain in which more than one pair of atoms of the alkyl chain form a double bond that is not part of an aromatic group. That is, a polyalkenyl chain contains from 2 to 8 R—C(R)═C(R)—R patterns, In one embodiment, R refers to the remaining portions of the alkenyl chain, which may be the same or different. The polyalkenyl moiety may be branched, or straight chain.

Non-limiting examples of polyalkenyl chains include: 3-methyl-1,3-butadienyl (1p), 3-methyl-6-(1-methylethenyl)-2-cyclohexen-1-yl (2g), (2E)-3,7-dimethyl-2,6-octadien-1-yl (geranyl) (2h), (2Z)-3,7-dimethyl-2,6-octadien-1-yl (neryl) (2i), 5-methyl-2-(1-methylethenyl)-4-hexen-1-yl (lavandulyl) (2j), (2E,6E)-3,7,11-trimethyl-2,6,10-dodecatrien-1-yl (farnesyl) (3b), (2E,6E,10E)-3,7,11,15-tetramethylhexadeca-2,6,10,14-tetraen-1-yl (geranylgeranyl) (4b), 8,11-heptadecadien-1-yl (16a).

16a

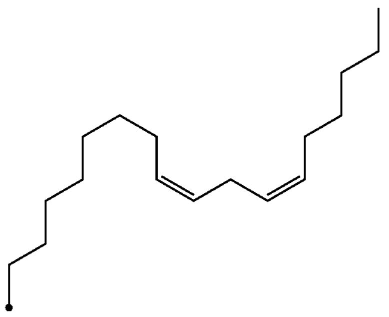

The polyalkenyl moiety containing two double bonds may be cyclic (in which case, it would also be known as a "cyclodialkenyl" group). Non limiting example of cyclodialkenyl groups include cyclopentadiene and cyclohexadiene groups. Polyalkenyl chains can be optionally substituted.

The term "substituted polyalkenyl" refers to:

1) a polyalkenyl chain as defined above, having 1, 2, 3, 4 or 5 substituents, (in some embodiments, 1, 2 or 3 substituents) selected from the group consisting of alkyl; alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)2-alkyl, —S(O)2-cycloalkyl, —S(O)2-heterocyclyl, —S(O)2-aryl and —S(O)2-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, and —S(O)n R<a>, in which R<a> is alkyl, aryl or heteroaryl and n is 0, 1 or 2;

One of the oxygen substituent of the polyalkenyl chain can be joined by single bonds to two adjacent carbon atoms of the same polyalkenyl chain, to form an epoxy group, i.e. a three-membered epoxide ring. One of the oxygen substituent of the polyalkenyl chain can from a five-membered aromatic ring with four carbon atoms of the same chain, resulting in a furan ring.

or 2) a polyalkenyl chain as defined above that is interrupted by 1-5 atoms (e.g. 1, 2, 3, 4 or 5 atoms) independently chosen from oxygen, sulfur and NR<a>, where R<a> is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, and —S(O)n R<a>, in which R<a> is alkyl, aryl or heteroaryl and n is 0, 1 or 2;

or 3) a polyalkenyl chain as defined above that has both 1, 2, 3, 4 or 5 substituents as defined above and is also interrupted by 1-5 atoms (e.g. 1, 2, 3, 4 or 5 atoms) as defined above;

or 4) a polyalkenyl chain as defined above in which one or more of the methylene group is replaced by a carbonyl group to give an oxo group.

or 5) a polyalkenyl chain as defined above in which one of the methylene group is replaced by a carbonyl group to give an oxo group, and has 1, 2, 3, 4 or 5 substituents as defined above, or is interrupted by 1-5 atoms (e.g. 1, 2, 3, 4 or 5 atoms) as defined above or has both 1, 2, 3, 4 or 5 substituents as defined above and is also interrupted by 1-5 atoms (e.g. 1, 2, 3, 4 or 5 atoms) as defined above.

Non limiting examples of polyalkenyl chains substituted by a hydroxy group, or containing a furan ring include: 5-hydroxy-3,7-dimethyl-2,6-octadienyl (2k), 6-hydroxy-3,7-dimethyl-2,7-octadien-1-yl (2l), 3,7-dimethyl-7-hydroxy-2,5-octadienyl (2m), 7-hydroxy-3,7,11-trimethyl-2,10-dodecadien-1-yl (3c), 3-methyl-6-[5-(2-methyl-1-propen-1-yl)-3-furanyl]-2-hexen-1-yl (3d).

Non limiting examples of linear or cyclized polyalkenyl chains in which one of the methylene group is replaced by a carbonyl group to give an oxo group, include: 3,7-dimethyl-5-oxo-2,6-octadienyl (2n), 1-oxo-2,4-octadien-1-yl (17a), 4,6-dihydroxy-6-methyl-3-oxo-1,4-cyclohexadien-1-yl (17b), (6-methyl-4-oxo-4H-pyran-2-yl)methyl (17c).

17a

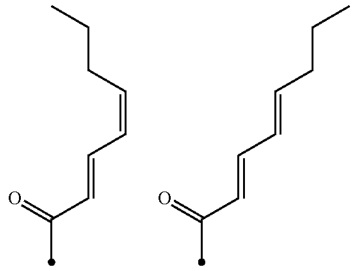

17b

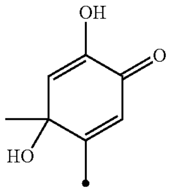

17c

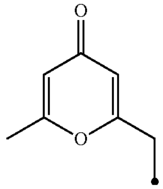

A non limiting example of a polyalkenyl chain substituted by an aryloxy group includes 8-(3,4-Dihydroxyphenyl)-4,7-octadien-1-yl (18a).

18a

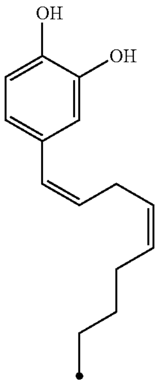

The term polyalkynyl refers to a chain in which more than one pair of atoms of the alkyl chain form a triple bond. That is, a polyalkynyl chain contains from 2 to 8 R—C≡C—R patterns, In one embodiment, R refers to the remaining portions of the alkynyl chain, which may be the same or different. Non-limiting example of a polyalkynyl chain include —CH2-CH2-C≡C—C≡CH. The "R" portion of the polyalkynyl moiety may be branched, straight chain, or cyclic.

The term "substituted polyalkynyl" refers to:

1) a polyalkynyl chain as defined above, having 1, 2, 3, 4 or 5 substituents, (in some embodiments, 1, 2 or 3 substituents) selected from the group consisting of alkyl; alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)2-alkyl, —S(O)2-cycloalkyl, —S(O)2-heterocyclyl, —S(O)2-aryl and —S(O)2-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, and —S(O)n R<a>, in which R<a> is alkyl, aryl or heteroaryl and n is 0, 1 or 2;

or 2) a polyalkynyl chain as defined above that is interrupted by 1-5 atoms (e.g. 1, 2, 3, 4 or 5 atoms) independently chosen from oxygen, sulfur and NR<a>, where R<a> is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, and —S(O)n R<a>, in which R<a> is alkyl, aryl or heteroaryl and n is 0, 1 or 2;

or 3) a polyalkynyl chain as defined above that has both 1, 2, 3, 4 or 5 substituents as defined above and is also interrupted by 1-5 atoms (e.g. 1, 2, 3, 4 or 5 atoms) as defined above;

or 4) a polyalkynyl chain as defined above in which one or more of the methylene group is replaced by a carbonyl group to give an oxo group.

or 5) a polyalkynyl chain as defined above in which one of the methylene group is replaced by a carbonyl group to give an oxo group, and has 1, 2, 3, 4 or 5 substituents as defined above, or is interrupted by 1-5 atoms (e.g. 1, 2, 3, 4 or 5 atoms) as defined above or has both 1, 2, 3, 4 or 5 substituents as defined above and is also interrupted by 1-5 atoms (e.g. 1, 2, 3, 4 or 5 atoms) as defined above.

The term "polyunsaturated" refers to a chain in which at least one pair of atoms of the alkyl chain form a double bond and one pair of atoms of the alkyl chain form a triple bond. That is, a polyunsaturated chain contains both R—C(R)═C(R)—R and R—C≡C—R patterns, In one embodiment, R refers to the remaining portions of the polyunsaturated chain, which may be the same or different and the total number of unsaturated bonds may vary from 2 to 8. Non-limiting examples this type of polyunsaturated chain include —CH2-CH═CH—C≡CH. The "R" portion of the polyunsaturated moiety may be branched, straight chain, or cyclic.

The term "substituted polyunsaturated" refers to:

1) a polyunsaturated chain as defined above, having 1, 2, 3, 4 or 5 substituents, (in some embodiments, 1, 2 or 3 substituents) selected from the group consisting of alkyl; alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)2-alkyl, —S(O)2-cycloalkyl, —S(O)2-heterocyclyl, —S(O)2-aryl and —S(O)2-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, and —S(O)n R<a>, in which R<a> is alkyl, aryl or heteroaryl and n is 0, 1 or 2;

or 2) a polyunsaturated chain as defined above that is interrupted by 1-5 atoms (e.g. 1, 2, 3, 4 or atoms) independently chosen from oxygen, sulfur and NR<a>, where R<a> is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, and —S(O)n R<a>, in which R<a> is alkyl, aryl or heteroaryl and n is 0, 1 or 2;

or 3) a polyunsaturated chain as defined above that has both 1, 2, 3, 4 or 5 substituents as defined above and is also interrupted by 1-5 atoms (e.g. 1, 2, 3, 4 or 5 atoms) as defined above;

or 4) a polyunsaturated chain as defined above in which one or more of the methylene group is replaced by a carbonyl group to give an oxo group.

or 5) a polyunsaturated chain as defined above in which one of the methylene group is replaced by a carbonyl group to give an oxo group, and has 1, 2, 3, 4 or 5 substituents as defined above, or is interrupted by 1-5 atoms (e.g. 1, 2, 3, 4 or 5 atoms) as defined above or has both 1, 2, 3, 4 or 5 substituents as defined above and is also interrupted by 1-5 atoms (e.g. 1, 2, 3, 4 or 5 atoms) as defined above.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can form part of a ring system. As used herein, the term "ring system" refers to two or more rings, In one embodiment, two or more of the rings are fused. The term "fused" refers to structures in which two or more rings share one or more bonds.

The term "halogen" may refer to a fluorine atom, a chlorine atom, a bromine atom or an iodine atom.

The term "glycoside" refers to a compound in which at least one sugar is bound to another functional group via a glycosidic bond. Typically the glycosidic chain can comprise 1 to 4 sugar units.

The term "glycosidic bond" refers to a bond formed between the hemiacetal or hemiketal group of a sugar and the chemical group of a compound. The chemical group can be —OH (O-glycoside), or —CR1R2R3 (C-glycoside).

The terms "acylated O-glycoside" and "acylated C-glycoside" refer to a compound in which at least one hydroxyl of the glycosidic chain is esterified by an organic acid. Typical examples or organic acid may comprise acetic, substituted benzoic, cinnamic (caffeic, ferulic, p-coumaric), and/or phenylpropanoic (dihydrocaffeic) acids.

The terms "sulfated O-glycoside" and "sulfated C-glycoside" refer to a compound in which at least one hydroxyl of the glycosidic chain is esterified by sulfuric acid.

The term "methylene dioxy" may refer to functional group with the structural formula R—O—CH2-O—R', connected to the rest of a molecule by two chemical bonds.

The term "analogue" as used herein is understood to refer to a compound having a structure similar to that of another one, but differing from it in respect of a certain component. A "derivative" is a compound that can be imagined to arise or is actually be synthesized from a parent compound by replacement of one or more atoms with another atom or group of atoms.

Compound or Composition Thereof

It is understood that according to certain embodiments, the compound of the invention or composition thereof may be a nutraceutical composition, pharmaceutical composition, functional food, functional nutrition product, medical food, medical nutrition product, or a dietary supplement.

The terms "nutraceutical" combines the words "nutrition" and "pharmaceutical". It is a food or food product that provides health and medical benefits, including the prevention and treatment of a condition, disorder, or disease. A nutraceutical is a product isolated or purified from foods that is generally sold in medicinal forms not usually associated with food. A nutraceutical is demonstrated to have a physiological benefit or provide protection against a condition, disorder, or disease. Such products may range from isolated nutrients, dietary supplements and specific diets to genetically engineered foods, herbal products, and processed foods such as cereals, soups, and beverages.

The term "nutraceutical" as used herein denotes usefulness in both nutritional and pharmaceutical fields of application. Thus, novel nutraceutical compositions can be used as supplements to food and beverages and as pharmaceutical formulations for enteral or parenteral application which may be solid formulations, such as capsules or tablets, or liquid formulations, such as solutions or suspensions.

The nutraceutical compositions according to the present invention may further contain protective hydrocolloids (such as gums, proteins, modified starches), binders, film-forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste-masking agents, weighting agents, jellifying agents, gel-forming agents, antioxidants and antimicrobials.

Moreover, a multi-vitamin and mineral supplement may be added to nutraceutical compositions of the invention to obtain an adequate amount of an essential nutrient, which is missing in some diets. The multi-vitamin and mineral supplement may also be useful for disease prevention and protection against nutritional losses and deficiencies due to lifestyle patterns.

The nutraceutical compositions of the invention may be in any galenic form that is suitable for administering to the body, especially in any form that is conventional for oral administration, e.g. in solid forms such as food or feed, food or feed premix, fortified food or feed, tablets, pills, granules, dragees, capsules and effervescent formulations such as powders and tablets, or in liquid forms, such as solutions, emulsions or suspensions as e.g. beverages, pastes and oily suspensions. The pastes may be incorporated in hard or soft shell capsules, whereby the capsules feature e.g. a matrix of (fish, swine, poultry, cow) gelatine, plant proteins or lignin sulfonate. Examples for other application forms are those for transdermal, parenteral or injectable administration. The dietary and pharmaceutical compositions may be in the form of controlled (delayed) release formulations.

Beverages encompass non-alcoholic and alcoholic drinks as well as liquid preparations to be added to drinking water and liquid food. Non-alcoholic drinks are e.g. soft drinks, sports drinks, fruit juices, teas and milk-based drinks. Liquid foods are e.g. soups and dairy products. The nutraceutical composition comprising the compound of the invention may be added to a soft drink, an energy bar, or a candy.

If the nutraceutical composition is a pharmaceutical formulation and the composition further contains pharmaceutically acceptable excipients, diluents or adjuvants then standard techniques may be used for their formulation, as e.g. disclosed in Remington's Pharmaceutical Sciences, 20th edition Williams & Wilkins, PA, USA. For oral administration, tablets and capsules are preferably used which contain a suitable binding agent, e.g. gelatine or polyvinyl pyrrolidone, a suitable filler, e.g. lactose or starch, a suitable lubricant, e.g. magnesium stearate, and optionally further additives.

"Functional food", "functional nutrition product", "medical food" and "medical nutrition product" relate to any healthy food claimed to have a health-promoting or disease-preventing property beyond the basic function of supplying nutrients. The general category of functional foods includes processed food or foods fortified with health-promoting additives, like "vitamin-enriched" products.

The terms "food," "food product" and "food composition" or "diet product" mean a product or composition that is intended for ingestion by an individual such as a human and provides at least one nutrient to the individual. The compositions of the present disclosure, including the many embodiments described herein, can comprise, consist of, or consist essentially of the elements disclosed herein, as well as any additional or optional ingredients, components, or elements described herein or otherwise useful in a diet.

A dietary supplement, also known as food supplement or nutritional supplement, is a preparation intended to supplement the diet and provide nutrients, such as vitamins, minerals, fibre, fatty acids, or amino acids that may be missing or may not be consumed in sufficient quantities in a person's diet. Some countries define dietary supplements as foods, while in others they are defined as drugs or natural health products. Supplements containing vitamins or dietary minerals are included as a category of food in the Codex Alimentarius, a collection of internationally recognized standards, codes of practice, guidelines and other recommendations relating to foods, food production and food safety. These texts are drawn up by the Codex Alimentarius Commission, an organization that is sponsored by the Food and Agriculture Organization of the United Nations (FAO) and the World Health Organization (WHO).

Compositions intended for an animal, include food compositions to supply the necessary dietary requirements for an animal, animal treats (e.g., biscuits), and/or dietary supplements. The compositions may be a dry composition (e.g., kibble), semi-moist composition, wet composition, or any mixture thereof. In one embodiment, the composition is a dietary supplement such as a gravy, drinking water, beverage, yogurt, powder, granule, paste, suspension, chew, morsel, treat, snack, pellet, pill, capsule, tablet, or any other suitable delivery form. The dietary supplement can comprise a high concentration of the UFA and NORC, and B vitamins and antioxidants. This permits the supplement to be administered to the animal in small amounts, or in the alternative, can be diluted before administration to an animal. The dietary supplement may require admixing, or can be admixed with water or other diluent prior to administration to the animal.

"Pet food" or "pet treat compositions" comprise from about 15% to about 50% crude protein. The crude protein material may comprise vegetable proteins such as soybean meal, soy protein concentrate, corn gluten meal, wheat gluten, cottonseed, and peanut meal, or animal proteins such as casein, albumin, and meat protein. Examples of meat protein useful herein include pork, lamb, equine, poultry, fish, and mixtures thereof. The compositions may further comprise from about 5% to about 40% fat. The compositions may further comprise a source of carbohydrate. The compositions may comprise from about 15% to about 60% carbohydrate. Examples of such carbohydrates include grains or cereals such as rice, corn, milo, sorghum, alfalfa, barley, soybeans, canola, oats, wheat, and mixtures thereof. The compositions may also optionally comprise other materials such as dried whey and other dairy by-products.

In some embodiments, the ash content of the pet food composition ranges from less than 1% to about 15%, and in one aspect, from about 5% to about 10%.

The moisture content can vary depending on the nature of the pet food composition. In a one embodiment, the composition can be a complete and nutritionally balanced pet food. In this embodiment, the pet food may be a "wet food", "dry food", or food of intermediate moisture content. "Wet food" describes pet food that is typically sold in cans or foil bags, and has a moisture content typically in the range of about 70% to about 90%. "Dry food" describes pet food which is of a similar composition to wet food, but contains a limited moisture content, typically in the range of about 5% to about 15% or 20%, and therefore is presented, for example, as small biscuit-like kibbles. In one embodiment, the compositions have moisture content from about 5% to about 20%. Dry food products include a variety of foods of various moisture contents, such that they are relatively shelf-stable and resistant to microbial or fungal deterioration or contamination. Also included are dry food compositions which are extruded food products, such as pet foods, or snack foods for companion animals.

Methods of Administration of Compound or Composition Thereof

The compound of the invention or composition thereof is preferably administered by oral administration. In some embodiments, the compound of the invention or composition thereof may be administered by intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

The composition of the invention can have an acute effect that can be seen in less than one month. Additionally or alternatively, the composition can have a longterm effect, and thus various embodiments comprise administration of the composition to the individual (e.g., orally) for a time period of at least one month; preferably at least two months, more preferably at least three, four, five or six months; most preferably for at least one year. During the time period, the composition can be administered to the individual at least one day per week; preferably at least two days per week, more preferably at least three, four, five or six days per week; most preferably seven days per week. The composition can be administered in a single dose per day or in multiple separate doses per day. In one embodiment, a single dose is not less than about 100 mg. In one embodiment, a single dose is not more than about 1000 mg. In one embodiment, a single dose is between about 100 mg and about 1000 mg.

AMPK Activation Terminology

As used herein, an "AMPK activator" refers to a compound that either increases the phosphorylation of downstream substrates of (phosphorylated or not) AMPK, and/or that increases the phosphorylation of AMPK.

As used herein, a "direct AMPK activator" refers to a compound that activates AMPK via direct interaction with at least one of its subunits.

Natural compounds activate AMPK almost exclusively through their ability to interfere with ATP production of the cell, typically by inhibiting mitochondrial respiration. As a consequence, this perturbs the adenine nucleotide levels within the cell and leads to activation of AMPK through AMP and ADP binding to the AMPK $\gamma$ subunit. This mechanism of AMPK activation has been termed "indirect" due to the fact that natural compounds do not directly bind to AMPK to achieve activation.

In contrast, AMPK can be "directly" activated by binding of molecules to the allosteric drug and metabolite (ADaM) binding site formed at the interface between the AMPK $\alpha$ subunit kinase domain and the AMPK $\beta$ subunit (Bultot, et al., (2016)Am J Physiol Endocrinol Metab 311(4): E706-e719; Ducommun et al., (2014)Am J Physiol Endocrinol Metab 306(6): E688-696; Ford et al., (2015) Biochem J 468(1): 125-132; O'Brien et al. (2015)Biochem J 469(2): 177-187).

In one preferred embodiment, the direct AMPK activator activates AMPK$\alpha2\beta1\gamma1$. As used herein, a condition, disorder, or disease "responsive to AMPK activation" refers to one in which the symptoms would be alleviated, or the course of which would be beneficially modified, through activation of AMPK, including without limitation, a metabolic disorder, diabetes, dyslipidemia, hypertension, being overweight, and obesity. For example, the metabolic disorder of diabetes is accompanied by conditions such as diabetic nephropathy or diabetic neuropathy which may be responsive to AMPK activation.

Medical Terminology

As used herein, the term "diabetes" includes insulin-dependent diabetes mellitus (i.e. IDDM, also known as type 1 diabetes) non-insulin-dependent diabetes mellitus (i.e. NIDDM, also known as type 2 diabetes), and prediabetes. Type 1 diabetes is the result of an absolute deficiency of insulin, the hormone which regulates glucose utilization. Type 2 diabetes often occurs in the face of normal, or even elevated levels of insulin and appears to be the result of the inability of tissues to respond appropriately to insulin. This is termed "insulin resistance". Most type 2 diabetic patients are also overweight or obese. One of the criteria for diagnosing diabetes is the fasting plasma glucose level. A diabetic subject has a fasting plasma glucose level of greater than or equal to 126 mg/dl. A prediabetic subject is someone suffering from prediabetes. A prediabetic subject is a subject with impaired fasting glucose (a fasting plasma glucose level of greater than or equal to 100 mg/dl and less than 126 mg/dl); or impaired glucose tolerance (a 2-hour plasma glucose level of ≥140 mg/dl and <200 mg/dl); or insulin resistance, resulting in an increased risk of developing diabetes. Prevention of type 2 diabetes includes treatment of prediabetes.

As used herein, the term "dyslipidemia" encompasses abnormal levels of any lipid fractions as well as specific lipoprotein abnormalities. For example, it refers to elevation of plasma cholesterol and/or elevation of triglycerides and/or elevation of free fatty acids and/or low high-density lipoprotein (HDL) level and/or high low-density lipoprotein (LDL) level and/or high very low-density lipoprotein (VLDL) level. Dyslipidemia may for example contribute to the development of atherosclerosis and ultimately symptomatic vascular disease including coronary heart disease. Dyslipidemia may or may not be associated with diabetes.

As used herein, the term "metabolic disorder" encompasses any abnormal chemical and enzymatic reactions disrupting normal metabolism due to environmental and genetic factors (environmental factors include physical activity, nutrition), leading to excessive levels or deficiency of certain substances and dysfunction of energy homeostasis. Non-limiting examples of metabolic disorders include diabetes, dyslipidemia, hypertension, being overweight, obesity, and any combination thereof.

As used herein, "AMPK-related diseases" includes pathologic or pathogenomic conditions in which the activation of AMPK provides a salutary effect. Examples of such diseases or conditions include obesity, diabetes, metabolic syndrome, acute inflammatory lung injury, heart disease, reperfusion ischemia, cancer, aging, retinal degeneration, cardiac hypertrophy, non-alcoholic fatty liver disease, hypertension, albuminuria, sporadic Alzheimer's disease, muscular dystrophy, and osteoarthritis. In addition, "AMPK-related conditions" include conditions where the activation of AMPK improves the condition associated with the primary "AMPK-related disease". For example, diabetic nephropathy (Salotto et al. (2017) J. Pharma and Expt Thera. 361:303-311) or diabetic neuropathy are "AMPK-related conditions" which may be associated with the "AMPK-related disease" of diabetes.

"Prevention" or "preventing" includes reduction of risk and/or severity of a condition, disorder, or disease.

The terms "treatment," "treating,", "treat", "attenuate" and "alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder, and include treatment of patients at risk of contracting a disease or suspected to have contracted a disease, as well as patients who are ill or have been diagnosed as suffering from a disease or medical condition. The term does not necessarily imply that a subject is treated until total recovery. These terms also refer to the maintenance and/or promotion of health in a subject not suffering from a disease but who may be susceptible to the development of an unhealthy condition. These terms are also intended to include the potentiation or otherwise enhancement of one or more primary prophylactic or therapeutic measure. The terms "treatment," "treat," "attenuate" and "alleviate" are further intended to include the dietary management of a disease or condition or the dietary management for prophylaxis or prevention a disease or condition. A treatment can be patient- or doctor-related.

Obesity, which is an excess of body fat relative to lean body mass, is a chronic disease that is highly prevalent in modern society. It is associated not only with a social stigma, but also with decreased life span and numerous medical problems, including adverse psychological development, coronary artery disease, hypertension, stroke, diabetes, hyperlipidemia, and some cancers, (see, e.g., Nishina, et al., Metab. 43:554-558, 1994; Grundy and Barnett, Dis. Mon. 36:641-731, 1990; Rissanen, et al., British Medical Journal, 301:835-837, 1990).

"Obesity related disorders" refers to those diseases or conditions where excessive body weight or high "body mass index (BMI)" has been implicated in the progression or suppression of the disease or condition. Representative examples of obesity related disorders include, without limitation diabetes, diabetic complications, insulin sensitivity, polycystic ovary disease, hyperglycemia, dyslipidemia, insulin resistance, metabolic syndrome, obesity, body weight gain, inflammatory diseases, diseases of the digestive organs, stenocardia, myocardial infarction, sequelae of stenocardia or myocardial infarction, senile dementia, and cerebrovascular dementia. See, Harrison's Principles of Internal Medicine, 13th Ed., McGraw Hill Companies Inc., New York (1994). Examples, without limitation, of inflammatory conditions include diseases of the digestive organs (such as ulcerative colitis, Crohn's disease, pancreatitis, gastritis, benign tumor of the digestive organs, digestive polyps, hereditary polyposis syndrome, colon cancer, rectal cancer, stomach cancer and ulcerous diseases of the digestive organs), stenocardia, myocardial infarction, sequelae of stenocardia or myocardial infarction, senile dementia, cerebrovascular dementia, immunological diseases and cancer in general.

The term "subject" or "individual" means any animal, including a human, that could benefit from one or more of the compounds, compositions or methods disclosed herein. Generally, the subject is a human or an avian, bovine, canine, equine, feline, hircine, lupine, murine, ovine or porcine animal. A "companion animal" is any domesticated animal, and includes, without limitation, cats, dogs, rabbits, guinea pigs, ferrets, hamsters, mice, gerbils, horses, cows, goats, sheep, donkeys, pigs, and the like. Preferably, the subject is a human or a companion animal such as a dog or cat. The term "elderly" in the context of a human means an age from birth of at least 60 years, preferably above 63 years, more preferably above 65 years, and most preferably above 70 years. The term "older adult" in the context of a human means an age from birth of at least 45 years, preferably above 50 years, more preferably above 55 years, and includes elderly subjects. For other animals, an "older adult" has exceeded 50% of the average lifespan for its particular species and/or breed within a species. An animal is considered "elderly" if it has surpassed 66% of the average expected lifespan, preferably if it has surpassed the 75% of the average expected lifespan, more preferably if it has surpassed 80% of the average expected lifespan. An elderly cat or dog has an age from birth of at least about 7 years.

As used herein, an "effective amount" is an amount that prevents a deficiency, treats a disorder, condition, or disease in a subject or, more generally, reduces symptoms, manages progression of the diseases or provides a nutritional, physiological, or medical benefit to the subject. The relative terms "improved," "increased," "enhanced" and the like refer to the effects of the composition disclosed herein relative to a composition lacking one or more ingredients and/or having a different amount of one or more ingredients, but otherwise identical.

General Terminology

As used herein, the singular forms "a," "an" and "the" include plural referents unless the context clearly dictates otherwise. Thus, for example, reference to "a component" or "the component" includes two or more components.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology include Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of pharmacology include Goodman and Gilman's The Pharmacological Basis of Therapeutics, 10th Ed., McGraw Hill Companies Inc., New York (2001). Standard medical terminology used herein has the meaning defined in Stedman's Medical Dictionary, 27th Edition, with veterinary medicine insert.

All percentages expressed herein are by weight of the total weight of the composition unless expressed otherwise. As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or compounds, but may also include additional features or compounds. The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the claims. Numerous specific details are set forth in the description in order to provide a thorough understanding of the present invention. The present invention may be practiced without some or all of these specific details.

In other instances, well known methods and protocols have not been described in detail, in order not to unnecessarily obscure the present invention.

U-2 OS cells were treated with varying concentrations of compound 1 for 30 mins at 37 C. Phosphorylation of ACC was assessed using the HTRF Cisbio (pACC kit). Results are displayed as the average fold increase in activation (±SEM) of 3 independent experiments. Compound 1 is 2,4-dihydroxy-3-[(1R,6R)-3-methyl-6-prop-1-en-2-ylcyclohex-2-en-1-yl]-6-pentylbenzoic acid, also known as Cannabidiolic acid, CAS number: 1244-58-2.

Figure 2:
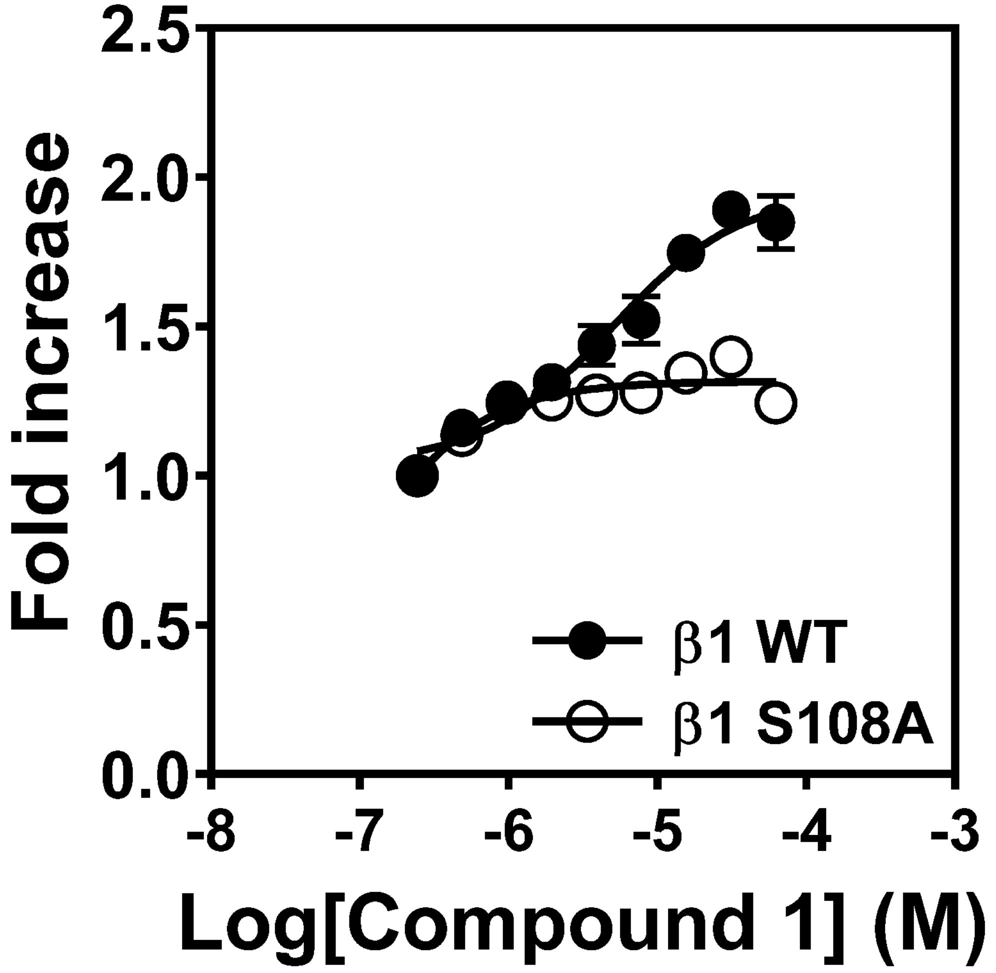

FIG. 2. Compound 1 did not activate AMPK in cells stably expressing an ADaM-binding site AMPK mutant (β1 S108A).

The β1 WT or β1 S108A mutant were stably expressed in AMPKβ1β2 double knockout cells and treated with varying concentrations of Compound 1 for 30 mins at 37 C. Phosphorylation of ACC was assessed using the HTRF Cisbio (pACC kit). Results are displayed as the average fold increase in activation (±SEM) of 3 independent experiments. Compound 1 is 2,4-dihydroxy-3-[(1R,6R)-3-methyl-6-prop-1-en-2-ylcyclohex-2-en-1-yl]-6-pentylbenzoic acid, also known as Cannabidiolic acid, CAS number: 1244-58-2.

Figure 3:
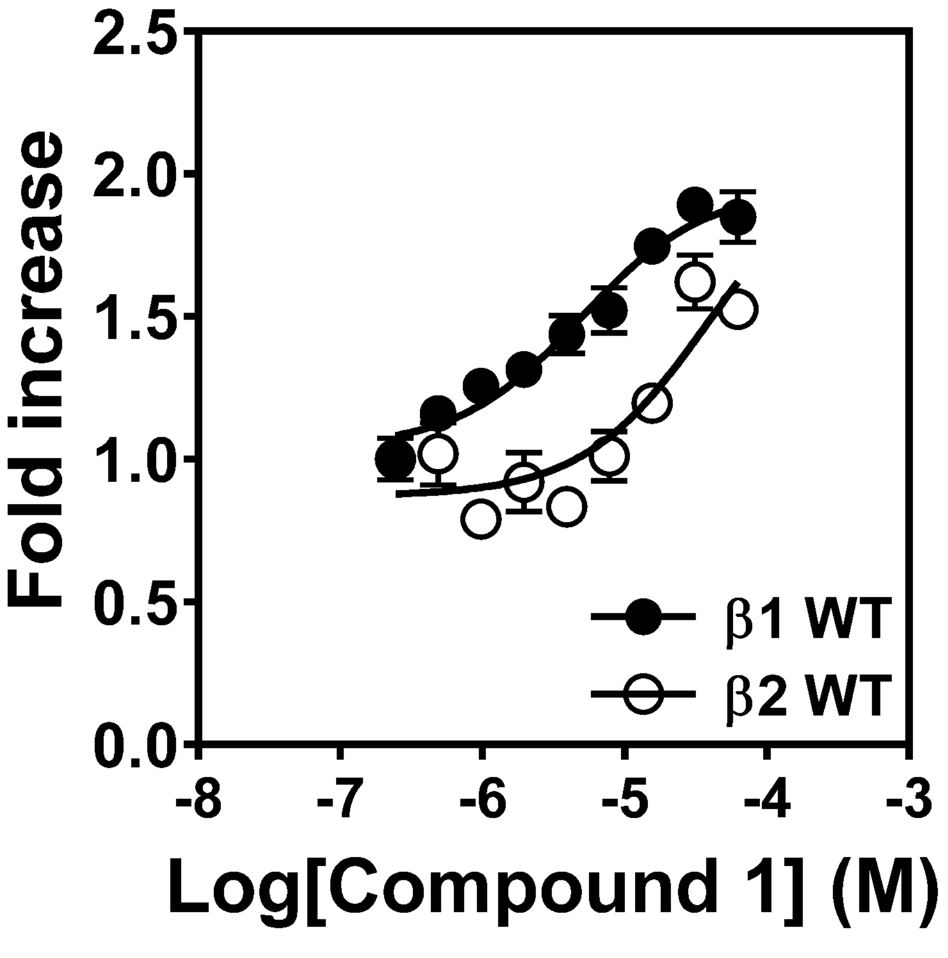

FIG. 3. Compound 1 had impaired activation of AMPK in cells stably expressing the β2 isoform.

U-2 OS cells AMPKβ1β2 double knockout cells stably expressing AMPK β1 or β2 were treated with varying concentrations of Compound 1 for 30 mins at 37 C. Phosphorylation of ACC was assessed using the HTRF Cisbio (pACC kit). Results are displayed as the average fold increase in activation (±SEM) of 3 independent experiments. Compound 1 is 2,4-dihydroxy-3-[(1R,6R)-3-methyl-6-prop-1-en-2-ylcyclohex-2-en-1-yl]-6-pentylbenzoic acid, also known as Cannabidiolic acid, CAS number: 1244-58-2.

Figure 4:
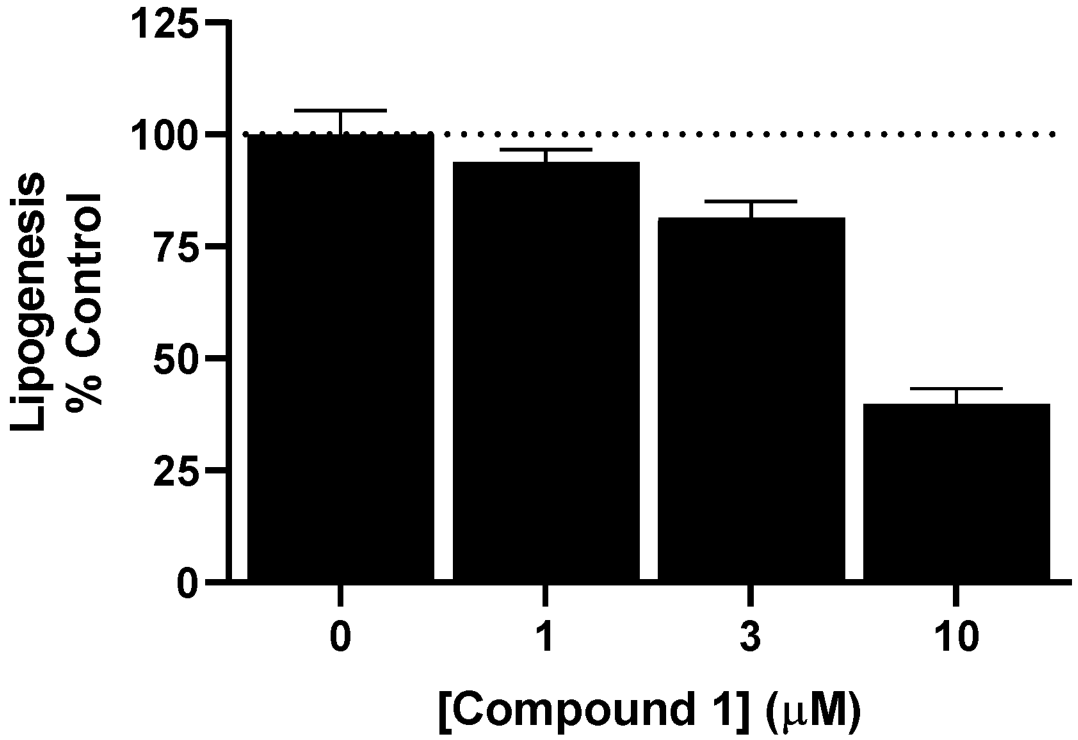

FIG. 4. Compound 1 displays a dose-dependent inhibition of lipogenesis in primary mouse hepatocytes.

Primary hepatocytes, cells were seeded at 600 K cells per well in a 6-well plate overnight. Media was replaced with fresh M199 media alone for 2 hours prior to incubation with varying concentrations of compound 1 for 1 h at 37 C, in the presence of [1-14C]-acetate. The incorporation of [14C] into fatty acids was determined in the lower organic layer after separation from the aqueous phase. The results are displayed as the percentage of lipogenesis compared to the no treatment control.

Compound 1 is able to inhibit lipogenesis in a dose-dependent manner.

EXAMPLES

Example 1

Compound 1 Increased the Phosphorylation of the AMPK Substrate, Acetyl-CoA Carboxylase (ACC), in U-2 OS Flp-In T-REx Mammalian Cells.

Numerous studies have demonstrated that a wide-range of different natural compounds activate AMPK. Typically, natural compounds do not activate AMPK by directly binding to the enzyme, but instead indirectly activate AMPK due to the fact that they can cause perturbations in mitochondrial respiration. This leads to a decrease in ATP levels of the cell and activation of AMPK through AMP/ADP binding to the nucleotide-binding site of the AMPK γ subunit.

In contrast, in the present invention, we have identified natural compounds that bind directly to AMPK through the allosteric drug and metabolite (ADaM) site formed at the interface between the AMPK α and AMPK β subunits. We have identified a new AMPK activator, which is part of the naturally occurring resorcylic acid chemical class, which directly activates AMPK in cells.

U-2 OS Flp-In T-REx cells were seeded at 50 K in a 96-well plate and left overnight at 37 C in DMEM GlutaMAX (Thermo Fisher Scientific) supplemented with 10% (vol/vol) FBS and 100 U/ml penicillin G, and 100 μg/ml streptomycin. Cells were treated for 30 mins with varying concentrations of Compound 1 in media lacking FBS and then cells were lysed in 50 μl of Cisbio lysis buffer #1 supplemented with blocking solution as per the manufacturer's protocol (Cisbio). Compound 1 is 2,4-dihydroxy-3-[(1R,6R)-3-methyl-6-prop-1-en-2-ylcyclohex-2-en-1-yl]-6-pentylbenzoic acid, also known as Cannabidiolic acid, CAS number: 1244-58-2.

Cells were lysed for 30 mins at room temperature before 16 μl of lysate was incubated with 4 μl of the HTRF antibodies (1:40 dilution of the acceptor and donor (p)ACC antibodies, as per the manufacturers protocol). Lysates were incubated overnight with the antibodies before 665 nm/620 nm ratio was determined using a MolecularDevices i3 plate reader (with a HTRF cartridge add-on).

Figure 1:
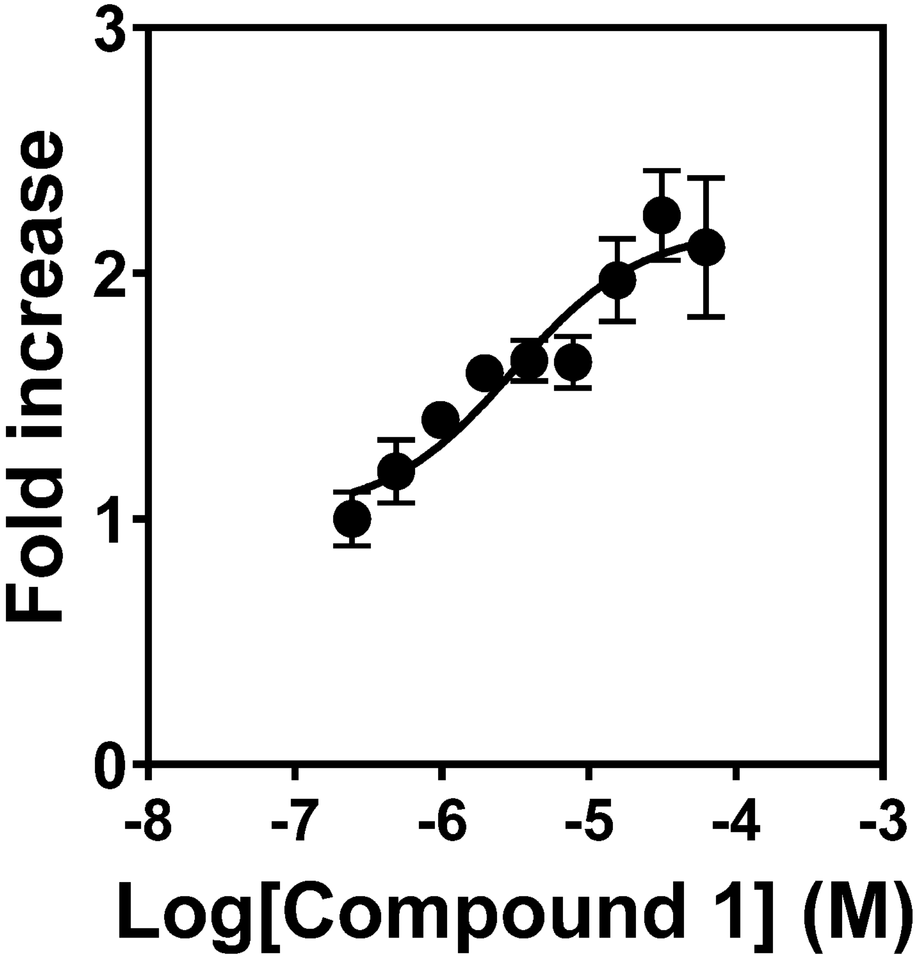
FIG. 1. Compound 1 increased the phosphorylation of the AMPK substrate, acetyl-CoA carboxylase (ACC), in U-2 OS Flp-In T-REx mammalian cells.

FIG. 1 shows that using the pACC HTRF assay kit (Cisbio), compound 1 increases the phosphorylation of the AMPK substrate, ACC, in a dose-dependent manner in U-2 OS Flp-In T-REx mammalian cells. Phosphorylation of ACC is widely used as a cellular read-out of AMPK activation.

Example 2

In Cells, Compound 1 Did not Activate AMPK Complexes Containing a Mutation at the Allosteric Drug and Metabolite (ADaM) Site in Cells (S108A).

Next we investigated whether the ability of compound 1 to activate AMPK was mediated through its ability to directly bind to the ADaM-binding site. Compound 1 is 2,4-dihydroxy-3-[(1R,6R)-3-methyl-6-prop-1-en-2-ylcyclohex-2-en-1-yl]-6-pentylbenzoic acid, also known as Cannabidiolic acid, CAS number: 1244-58-2.

A MPKβ1/β2 double knockout U-2 OS Flp-In™ T-Rex™ cell lines were generated by Horizon Discovery (Cambridge, UK). Cells were genotyped and analysed by western blotting to confirm that there was a complete knockout of AMPKβ1/β2. We took these AMPKβ1/β2 double knockout cells, and re-introduced the expression of human β1 wild-type (WT) or a β1 Serine 108 to alanine mutation (S108A). This was achieved using the Flp-In™ system (Invitrogen) present in this cell line and stable cells expressing β1 WT or a β1 S108A mutant were generated according to the manufacturers' protocols. Re-expression of the β1 subunit was confirmed by western blot analysis. Mutation of β1 S108A has previously been shown to interfere with regulation of AMPK by compounds binding to the allosteric drug and metabolite (ADaM) binding site formed at the interface between the β subunit carbohydrate binding module (CBM) and the α subunit kinase domain. In contrast, activators through work through nucleotide binding in the AMPK γ subunit can still regulate the β1 S108A mutant comparable to β1 WT activation.

Cells stably expressing β1 WT or a β1 S108A mutant were treated with varying concentrations of Compound 1 and subjected to the pACC HTRF (Cisbio) assay to determine the level of phosphorylation of the AMPK substrate, ACC, in cell lysates, as in example 1. As shown in FIG. 2, Compound 1 was able to dose-dependently increase pACC in cells stably expressing the β1 WT subunit. In contrast, Compound 1 was not able to increase pACC in cells expressing the β1 S108A mutant. This suggests that Compound 1 activates AMPK by binding to the ADaM pocket of AMPK.

Example 3

In Cells, Compound 1 Impaired Activation of β2-Containing AMPK Complexes.

We took AMPKβ1/β2 double knockout cells, and re-introduced the expression of human β1 WT or β2 WT isoforms. Re-expression of the β1 and β2 subunits was confirmed by Western blot analysis and were shown to be expressed to a similar extent. Cells stably expressing β1 WT or β2 were treated with varying concentrations of compound 1 and subjected to the pACC HTRF (Cisbio) assay to determine the level of phosphorylation of the AMPK substrate, ACC, in cell lysates, as in example 1. As shown in FIG. 3, compound 1 was able to dose-dependently increase pACC in cells stably expressing β1 WT. In contrast, there was an impaired ability of compound 1 to increase pACC in cells expressing the β2 WT isoform. This activation profile is characteristic of activators that bind to the ADaM site and consistent with previous studies showing that ADaM-site activators have poorer activation of β2-containing complexes in vitro and in cells. Taken together, we show that in cells, compound 1 activates AMPK by binding to the ADaM pocket of AMPK separate from the nucleotide-binding site in the AMPKγ subunit.

Taken together, we show for the first time that a new resorcylic acid compound (compound 1), activates AMPK by binding to the ADaM pocket of AMPK, which is separate from the nucleotide-binding site in the AMPKγ subunit. Compound 1 is 2,4-dihydroxy-3-[(1R,6R)-3-methyl-6-prop-1-en-2-ylcyclohex-2-en-1-yl]-6-pentylbenzoic acid, also known as Cannabidiolic acid, CAS number: 1244-58-2.

Example 4: Compound 1 Displays a Dose-Dependent Inhibition of Lipogenesis in Primary Hepatocytes Hepatocyte isolation: The liver was first perfused with 50 ml perfusion buffer (Krebs-Hepes buffer with 0.5 μM EDTA), followed with 50 ml collagenase A buffer (Krebs-Hepes buffer with 5 mM CaCl2) and 0.5 mg/ml collagenase). After passage through a 100 μm mesh, the cell solution was washed several times with cold media and finally the cell culture pellet was resuspended in culture medium (medium 199 (M199)+GlutaMAX, 100 U/ml penicillin G, and 100 μg/ml streptomycin, 0.1% (wt/vol) BSA, 10% FCS, 10 nM insulin, 200 nM triiodothyronine and 500 nM dexamethasone). Hepatocytes were left to attach (3-4 h) and cultured overnight in M199 supplemented with antibiotics and 100 nM dexamethasone. Cells were used for experiments the following morning.

For lipogenesis measurements in primary hepatocytes, cells were seeded at 600 K cells per well in a 6-well plate overnight. Media was replaced with fresh M199 media alone for 2 hours prior to incubation with varying concentrations of compound 1 for 1 h at 37 C, in the presence of [1-14C]-acetate. The incorporation of [14C] into fatty acids was determined in the lower organic layer after separation from the aqueous phase. The results are displayed as the percentage of lipogenesis compared to the no treatment control.

Lipogenesis is controlled by the AMPK substrate ACC, and phosphorylation and inhibition of ACC by AMPK, leads to a decrease in lipogenesis. Lipogenesis was measured in primary hepatocytes by determining the incorporation of 14C-labelled acetate into fatty acids. Lipogenesis was monitored in the presence or absence of varying concentrations of compound 1 for 1 h at 37 C. The results shown in FIG. 4, show that compound 1 is able to inhibit lipogenesis in a dose-dependent manner. This observation is consistent with its ability to activate AMPK in hepatocytes, which leads to the phosphorylation and inhibition of ACC. These data are also consistent with the ability of compound 1 to activate AMPK in both a cell line and primary hepatocytes.

The invention claimed is:

1. A method for activation of AMPK for curative treatment of non-alcoholic fatty liver disease in an individual having the non-alcoholic fatty liver disease, the method comprising administering cannabidiolic acid CAS number 1244-58-2 to the individual.

2. The method according to claim 1, wherein the activation of AMPK is through a direct activation mechanism.

3. The method according to claim 1, wherein the activation of AMPK is in muscle, liver and/or kidney tissues.

4. The method according to claim 1, wherein the AMPK comprises an α2 subunit, a β1 subunit, and a γ1 subunit.

5. The method according to claim 1, wherein the cannabidiolic acid is orally administered in a composition, and the composition is a food, beverage, or dietary supplement.

6. The method according to claim 1, wherein the cannabidiolic acid is administered in a composition, and the composition further comprises a pharmaceutically acceptable carrier.

7. The method according to claim 1, wherein the the cannabidiolic acid is orally administered.

8. The method according to claim 1, wherein the cannabidiolic acid is orally administered in a tablet or capsule.

* * * * *